United States Patent
Ghosh

(10) Patent No.: US 7,211,648 B2
(45) Date of Patent: May 1, 2007

(54) TOPICAL COMPOSITIONS FOR THE TREATMENT, PROTECTION AND RESTORATION OF SKIN AND CONNECTIVE TISSUES

(75) Inventor: Peter Ghosh, Fairlight (AU)

(73) Assignee: Institute of Nutraceutical Research Pty. Ltd., New South Wales (AU)

( * ) Notice: Subject to any disclaimer, the term of this patent is extended or adjusted under 35 U.S.C. 154(b) by 0 days.

(21) Appl. No.: 11/130,470

(22) Filed: May 16, 2005

(65) Prior Publication Data

US 2006/0040851 A1 Feb. 23, 2006

Related U.S. Application Data

(63) Continuation-in-part of application No. 10/896,546, filed on Jul. 22, 2004, which is a continuation-in-part of application No. PCT/AU03/00061, filed on Jan. 23, 2003.

(30) Foreign Application Priority Data

Jan. 23, 2002 (AU) ........................ PS0112
Mar. 12, 2002 (AU) ........................ PS1054

(51) Int. Cl.
*C07K 1/00* (2006.01)
(52) U.S. Cl. ................................... 530/350
(58) Field of Classification Search ................. 530/350; 514/12
See application file for complete search history.

(56) References Cited

U.S. PATENT DOCUMENTS 6,147,059 A * 11/2000 Falk et al. ................ 514/54
2001/0026790 A1 * 10/2001 Gers-Barlag et al. ......... 424/59

FOREIGN PATENT DOCUMENTS

WO   WO 200185192   * 11/2001

OTHER PUBLICATIONS

Katona G., A clinical trial of glycosaminoglycan-peptide complex ('Rumalon') in pateints with osteoarthritis of the knee, Curr. Medical Research, 1987, vol. 10, p. 625-633.*
Parthasarathy et al., Isolation and Characterization of Low Molecular Weight Chondroitin Sulfate Proteoglycan from Rabbit Skeletal Muscle, Biochemistry, 1987, 26, p. 3149-3156.*

* cited by examiner

*Primary Examiner*—Robert A. Wax
*Assistant Examiner*—Agnes B. Rooke
(74) *Attorney, Agent, or Firm*—Frommer Lawrence & Haug LLP; Thomas J. Kowalski; Angela M. Collison

(57) ABSTRACT

The invention relates to uses of GAG-peptide complexes and polypeptides obtained from connective tissue albeit indirectly which are substantially free of DNA for the treatment, protection and restoration of skin and connective tissues. The invention provides a topical composition comprising at least on GAG-peptide complex comprising two or three GAG-chains.

9 Claims, 19 Drawing Sheets

Bovine Trachael Cartilage
– before [A & C] and after treatment [B & D]

[A] TB stain = Sulfated GAGs

[B] TB stain = Sulfated GAGs

[C] MassonTC stain = Collagen

[D] MassonTC stain = Collagen

ChSA ($A_{260}$=0.39; $A_{280}$=0.21)

CaP ($A_{260}$=0.12; $A_{280}$=0.11)

NaP ($A_{260}$=0.13; $A_{280}$=0.12)

H2OP ($A_{260}$=0.20; $A_{280}$=0.19)

TOPICAL COMPOSITIONS FOR THE TREATMENT, PROTECTION AND RESTORATION OF SKIN AND CONNECTIVE TISSUES

REFERENCE TO RELATED APPLICATIONS

This application is a continuation-in-part of U.S. Ser. No. 10/896,546 filed Jul. 22, 2004, which is a continuation-in-part of International Patent Application PCT/AU03/00061 filed Jan. 23, 2003 and published as WO 03/062279 on Jul. 31, 2003, and claims priority from Australian Patent Applications PS 0112 filed Jan. 23, 2002 and PS 1054 filed Mar. 12, 2002. The present application also claims priority from PCT/AU05/000044 filed Jan. 14, 2005. Mention is also made of Provisional Application No. AU 2004900250 filed Jan. 16, 2004, from which PCT/AU05/000044 claims priority. Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. Patent law; namely, that these terms are closed ended.

TECHNICAL FIELD

The invention relates to uses of GAG-peptide complexes and polypeptides substantially free of DNA obtained either directly from connective tissue, or after further processing, for the treatment, protection and restoration of skin and connective tissue in a person in need thereof.

BACKGROUND OF THE INVENTION

1. Background Art

The proteoglycans of articular cartilage consist of a protein core to which several hundred GAG chains are covalently attached. The major GAG substituents of the proteoglycans of articular cartilage are the chondroitin sulfates (ChS). In adult cartilage Ch-6-S is more abundant than the corresponding 4-sulfated isomer (Ch-4-S) which predominates in articular cartilage of very young animals. Another GAG covalently attached to the core protein of proteoglycans are the keratan sulfates (KS). These are of smaller molecular weight than the ChS (5000–8000 Da) and are predominately clustered in a domain at the N-terminal end of the proteoglycan core protein known as the G1–G2 interglobular domain. Within the extracellular matrix of articular cartilage hydrated proteoglycan complexes are entrapped in the form of macromolecular aggregates by a three dimensional network of Type II collagen fibres. This unique structural organisation of proteoglycan, water and a fibrous collagen network which is anchored in the subchondral bone plate confers to articular cartilage the biomechanical properties of resilience necessary for normal biomechanical function.

Products of cartilage breakdown in vivo, particularly in arthritis affected joints, have been shown to be antigenic and when released into synovial fluid may provoke synovial inflammation. Once established, synovial inflammation, can alter the metabolism of resident synoviocytes, which are the major cellular source of synovial hyaluronic acid in joints. Inflammatory mediators released from local macrophage and infiltrating leukocytes can also promote increased vascular permeability and the dilution of synovial fluid by plasma fluid, thereby decreasing local hyaluronic fluid concentration. This dilution of hyaluronic acid coupled with a reduction in its molecular size due to abnormal synthesis by synoviocytes results in a substantial decrease in the rheological properties of synovial fluid and consequently its ability to lubricate and protect articular cartilage. Macrophage of the synovium, together with the leukocytes which enter the synovial cavity due to the local inflammation, are also an abundant source of cytokines [eg interleukin-1 (IL1)], procoagulant factors, proteinases and oxygen-derived free radicals including nitric oxide radical. While much of the excess proteolytic activity released into synovial fluid is abrogated by the endogenous inhibitors present, cytokines and free radicals can freely diffuse into cartilage and down-regulate proteoglycans and collagen synthesis by chondrocytes. These proinflammatory mediators can also initiate the production of catabolic proteinases, cytokines and free radicals such as nitric oxide by the cartilage cells which contribute to further articular cartilage matrix destruction via autocrine and paracrine pathways.

Accordingly, in arthritic diseases such as osteoarthritis, multiple tissues of the joint are affected and their excessive breakdown and the concomitant elicitation of an inflammatory reaction can lead not only to the progression of the disease state but also the initiation of symptoms the most common being pain and impairment of joint function.

Glucosamine and chondroitin sulphate (ChS) which are both constituents of cartilage proteoglycans are widely used products for the management of arthritic disease. Commercially available glucosamine is generally isolated from the chitosan present in the exoskeleton of crustacea. By contrast, commercially available chondroitin sulfates are normally manufactured from bovine tissues such as lung and trachea by hydrolysis of the GAG protein core linkage of the cartilage proteoglycan using either chemical or enzymatic procedures. The negatively charged water soluble ChS may be separated and purified from the proteins and peptides also generated by the hydrolysis of cartilage by multiple precipitations with acetone, aliphatic alcohols or the formation of water insoluble complexes with quaternary ammonium salts such as cetyl pyridinium chloride (CPC). However, none of these methods readily remove the contaminating nucleic acids (DNA and RNA) and other intracellular components also released during the chemical or enzymatic disruption of cartilage since these macromolecules are also anionic and would co-precipitate with the anionically charged ChS.

While the consequences of long term human consumption of bovine or other animal nucleic acids in commercial ChS preparations sold as nutraceuticals or food supplements is presently unknown, it should be noted that these intracellular anionic macromolecules are strongly bound to or form complexes with retroviruses and heat/protease resistant prion proteins which have been implicated in the spread of transmissible spongiform encephalopathies variants such as Creutzfeld-Jakob disease, kuru, Gerstmann-Straussler-Scheiner syndrome in humans, scrapie in sheep and goats, and bovine spongioform encaphalopathies in cattle. These intracellular entities could therefore be consumed by the subject in appreciable amounts when they comply with the manufactures recommended dosage of one or more grams of ChS daily for the suppression of the symptoms arising from osteoarthritis and related conditions.

2. General

As used in the specification and claims, the singular form "a," "an" and "the" include plural references unless the context clearly dictates otherwise. For example, the term "a fungal pathogen" includes a plurality of fungal pathogens, including mixtures thereof.

As used herein the term "derived" or "derived from" shall be taken to indicate that a specified integer are obtained from a particular source albeit not necessarily directly from that source.

A "composition" is intended to mean a combination of active agent and another compound or composition, inert (for example, an excipient) or another active.

Unless the context requires otherwise or specifically stated to the contrary, integers, steps, or elements of the invention recited herein as singular integers, steps or elements clearly encompass both singular and plural forms of the recited integers, steps or elements.

The embodiments of the invention described herein with respect to any single embodiment shall be taken to apply mutatis mutandis to any other embodiment of the invention described herein.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally equivalent products, compositions and methods are clearly within the scope of the invention, as described herein.

SUMMARY OF THE INVENTION

In work leading to the present invention, the inventor investigated methods of obtaining GAG-peptide complexes and polypeptides substantially free of DNA and uses thereof from connective tissue (see PCT/AU03/00061 and PCT/AU2005/00044). PCT/AU03/00061 provides a novel method for obtaining connective tissue derived compositions comprising GAG-peptide complexes and polypeptides substantially free of DNA by a method of autolysis which is essentially non-disruptive to the connective tissue used. The inventor found that GAG-peptide complexes produced by the inventive method include GAG-peptide complexes which comprise 2 or 3 GAG chains and that a connective tissue derived composition (referred to in PCT/AU03/00061 as a "Peptican") or mixture comprising at least one of these GAG-peptide complexes and at least one polypeptide is useful in the treatment, protection and restoration of connective tissue in inflammatory and degenerative tissue disorders. PCT/AU2005/00044 discloses a novel method for obtaining the GAG-peptide complex alone or in a mixture wherein the method comprises "limited hydrolysis". PCT/AU2005/00044 also discloses that a connective tissue derived composition comprising the GAG-peptide complex alone or in combination with a polypeptide is useful for preventing the onset of inflammation and arthritic disease.

In ongoing work, the present inventor has now found that an effective skin care benefit or subdermal tissue benefit may be obtained by the application of a topical composition to a subject, the composition comprising a connective tissue derived composition comprising at least one GAG-peptide complex either alone or in combination with one or more polypeptides.

Accordingly, in one aspect the present invention provides a topical composition comprising a connective tissue derived composition comprising one or more GAG-peptide complexes in combination with a dermatological acceptable vehicle, wherein at least one GAG-peptide complex comprises 2 or 3 GAG chains.

Preferably, the connective tissue derived composition further comprises at least one connective tissue derived polypeptide.

Preferably, the topical composition provides a skin care benefit and/or a subdermal tissue benefit.

In one embodiment the skin care benefit is cosmetic. In an alternate embodiment the skin care benefit is therapeutic and optionally cosmetic. The term "cosmetic" as used herein refers to serving an aesthetic purpose in treating or beautifying the body, while the term "therapeutic" refers to tending to treat an ailment, to cure or restore to health.

In another aspect of the present invention there is provided a method of providing at least one skin care benefit and/or subdermal tissue benefit to a subject in need thereof, the method comprising applying to the skin a topical composition as described herein.

In one preferred embodiment the skin care benefit comprises, for example, treating and/or decreasing wrinkling, sagging, dryness, irritation, inflammation, swelling, scarring of the skin, reducing the effects of ageing and/or photodamage of the skin; boosting collagen deposition in skin, enhancing tissue repair and healing; improving skin texture, smoothness and/or firmness.

In another embodiment the skin care benefit or subdermal tissue benefit is therapeutic, such as for example, treating and/or reducing inflammation, trauma, damage, irritation, allergic reaction, swelling, pain or stiffness of a subdermal tissue, more particularly a connective tissue.

The present invention also encompasses the use of the connective tissue derived composition for providing at least one skincare benefit or subdermal tissue benefit in a subject in need thereof.

Accordingly in a further aspect of the invention there is provided the use of a connective tissue derived composition comprising one or more GAG-peptide complex in a topical composition for providing at least one skin care benefit or subdermal tissue benefit to a subject in need thereof, wherein at least one GAG-peptide complex comprises two or three GAG-chains.

Advantageously, in several aspects and embodiments of the invention, the inventive topical compositions, methods and uses provide cosmetic skin care benefits and preferably anti-ageing benefits which result in the promotion of smooth and supple skin with improved elasticity and a reduced or delayed appearance of wrinkles and aged skin, with improved skin colour. A general improvement in the appearance, texture and condition in particular with respect to the radiance, clarity and general youthful appearance of skin is preferably achieved. The physical signs of ageing, such as wrinkles, lines and/or sagging are preferably delayed or reduced. Generally, the quality of skin is enhanced and its appearance and texture is improved by preventing or reducing wrinkling and increasing flexibility, firmness, smoothness, suppleness and elasticity of the skin. The compositions, methods and uses according to the invention may be useful for treating skin that is already in a wrinkled, aged and/or photodamaged condition or for treating youthful skin to prevent or reduce those aforementioned undesirable changes due to the normal ageing/photo-ageing process.

In other aspects and embodiments, the inventive topical compositions, methods and uses provide therapeutic benefits to a subject in need thereof including reducing, delaying and/or preventing the undesirable symptoms of inflammation and arthritis of a subdermal tissue, preferably a connective tissue.

Methods for obtaining a connective tissue derived composition comprising a GAG-peptide complex and/or polypeptide for use in the present invention are described, for example in PCT/AU03/00061, PCT/AU2005/000044, and PCT/AU2004/000788 (in the name of the Inventor/Applicant) which are incorporated herein by reference.

In one embodiment, the method for recovering a connective tissue derived composition comprising a GAG-peptide complex and polypeptide comprises
(i) incubating a connective tissue in an autolysis medium that provides a buffered pH range of between about pH 2.5 and about pH 8.5 for a time and under conditions sufficient to release at least one GAG-peptide complex comprising 2 or 3 GAG chains and at least one polypeptide; and
(ii) recovering a mixture comprising at least one GAG-peptide complex and at least one polypeptide from the autolysis medium.

In another embodiment the method for recovering a connective tissue derived composition comprising the GAG-peptide complex and polypeptide mixture comprises
(i) incubating a connective tissue in a hydrolysis medium for a time and under conditions sufficient to release at least one GAG-peptide complex comprising 2 or 3 GAG chains and at least one polypeptide; and
(ii) recovering a mixture comprising at least one GAG-peptide complex and at least one polypeptide from the hydrolysis medium.

In one embodiment the hydrolysis medium is an alkaline hydrolysis medium, which is preferably aqueous. Preferably the alkaline hydrolysis medium comprises a concentration of alkali of about 0.1–2.0% w/v. In a preferred embodiment the concentration of alkali is about 0.1%, 0.2%, 0.4%, 0.8%, 1.0%, 1.5% or 2%.

Preferably the method for recovering a mixture comprising a GAG-peptide complex and polypeptide from the hydrolysis medium comprises neutralization of the recovered mixture. More preferably, the mixture is neutralised by the addition of ascorbic acid or acetic acid.

According to a further embodiment, the connective tissue derived composition comprising the recovered GAG-peptide complex and polypeptide mixture is subjected to fractionation to select a fraction comprising at least one GAG-peptide complex of a preferred molecular weight of greater than 1000 Da.

Accordingly, in one embodiment the method for recovering the connective tissue derived composition comprising a mixture of GAG-peptide complexes and polypeptides comprises
(i) incubating a connective tissue in an autolysis medium that provides a buffered pH range of between about pH 2.5 and about pH 8.5 for a time and under conditions sufficient to release a mixture of at least one GAG-peptide complex comprising 2 or 3 GAG chains and at least one polypeptide;
(ii) recovering a mixture comprising at least one GAG-peptide and at least one polypeptide from the autolysis medium and
(iii) fractioning the mixture to obtain a GAG-peptide and a polypeptide having a molecular weight of greater than about 1000 Da.

In another embodiment the method for recovering the connective tissue derived composition comprising a GAG-peptide complex and polypeptide mixture comprises
(i) incubating a connective tissue in an aqueous alkaline hydrolysis medium for a time and under conditions sufficient to release at least one GAG-peptide complex comprising 2 or 3 GAG chains and at least one polypeptide;
(ii) recovering a mixture comprising at least one GAG-peptide complex and at least one polypeptide from the hydrolysis medium and
(iii) fractioning the mixture to obtain a GAG-peptide and a polypeptide having a molecular weight of greater than about 1000 Da.

In yet another embodiment the connective tissue derived GAG-peptide complex and polypeptide mixture is recovered and one or more GAG-peptide complexes are separated from the polypeptides. Accordingly in one embodiment, the methods described herein further comprise separating the polypeptide from one or more GAG-peptide complex and recovering a composition comprising at least one GAG-peptide complex comprising 2 or 3 GAG chains, and optionally recovering the polypeptide.

It is to be understood that in addition to comprising a GAG-peptide complex, the composition of the invention can further comprise one or more polypeptides separated and recovered according to the methods of the invention or by alternate means. The 4 present invention clearly extends to a composition comprising a GAG-peptide complex alone or in combination with a polypeptide derived from any source. In a preferred embodiment the polypeptide is connective tissue derived. Preferably the connective tissue derived polypeptide is obtained by a method described herein.

Furthermore, the composition can comprise a further connective tissue derived material which is preferably obtained by a method described herein. Connective tissue derived materials that may be present include, for example, collagens, non-collagenous proteins and large aggregating proteoglycans (PGs). Connective tissues also generally contain small proteoglycans such as heparan sulfate, the dermatan sulfate (chondroitin sulfate B) containing PGs known as decorin and byglycan, and the KS bearing PG known as fibromodulin as well as breakdown products arising from enzymatic and free radical cleavage of the matrix proteoglycans (small and large), GAGs (ChS, HA, Heparin sulfates, KS) and proteins. Some connective tissues such as skin and ligament contain elastin and others may contain lipids and fats. In the cells, of course, there is DNA and RNA and all tissues contain water and inorganic ions such as $Na^+$, $K^+$, $Ca^{++}$, $Cl^-$, $HCO_3^-$ etc.

Fractions (1.0 mL) were collected and assayed for the levels of sulfated glycosaminoglycans using the method of Farndale et al, 1986 [Farndale R W, Buttle D J and Barrett A J. Improved quantitation and discrimination of sulfated glycosaminoglycans by use of dimethylmethylene blue. Biochim. Biophys. Acta: 883, 173–177, 1986]. The profile represented by filled boxes corresponds to GAG-PLH, the filled triangles to INR-918R and thr filled circles to INR-919R. Vo and Vt indicate the void and total volumes of the column respectively.

Figure 19:
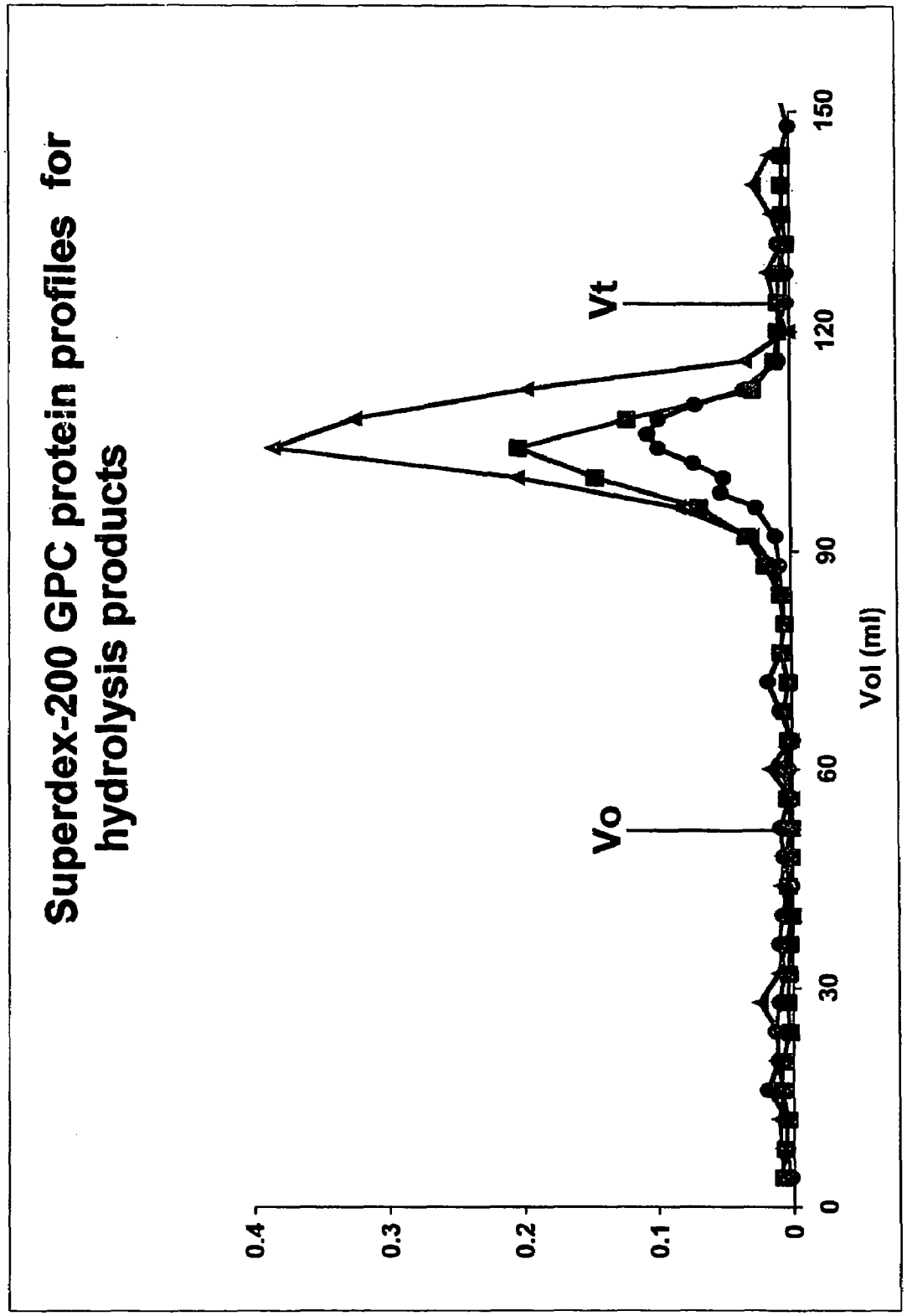

FIG. 19 provides a Superdex-200 gel permeation chromatographic (GPC) profile of glycosaminoglycan peptides isolated from hydrolysis of bovine tracheal cartilage or the residue remaining from the preparation of Calcium Peptacan as described previously. The column was eluted with 0.25M NaCl at a flow rate of 11.0 mL/minute. Fractions (1.0 mL) were collected and assayed for the levels of proteins/peptides using the BCA method described in the text. The profile represented by filled boxes corresponds to GAG-PLH, the filled triangles to INR-918R and the filled circles to IR-919P, Vo and Vt indicate the void and total volumes of the column respectively. Previous calibration of the column with molecular weight protein standards suggested that the GAG-PLH and INR-918R preparations had a weight averaged molecular weights of about 20,000 Da, while the proteins in INR-919R corresponded to 17,000 Da.

DETAILED DESCRIPTION

Connective Tissue Derived Composition

The present invention provides a topical composition comprising a connective tissue derived composition comprising one or more GAG-peptide complex in combination with a dermatological acceptable vehicle, wherein at least one GAG-peptide complex comprises 2 or 3 GAG-chains.

In one embodiment, the connective tissue derived composition comprises mixtures of GAG-peptides having various GAGs and numbers of GAGs attached to a peptide, wherein at least one of the GAG-peptide complexes comprises two or three GAGs attached to a peptide. In a preferred embodiment, two GAGs are attached to the peptide. In an alternate embodiment three GAG chains are attached to the peptide. The connective tissue derived composition may also include a single GAG chain attached to a peptide or a single GAG chain such as chondroitin sulfate. Alternatively or addition to single GAG chains and single chain GAG-peptides the connective tissue derived composition further comprises GAG peptide complexes comprising more than three GAG chains.

Preferably, the connective tissue derived composition comprises at least one connective tissue derived polypeptide or peptide. Accordingly, in one embodiment of the invention the connective tissue derived composition comprises at least one GAG-peptide complex comprising two or three GAG chains and at least one connective tissue derived polypeptide.

In alternate embodiments of the invention, the connective tissue derived composition further comprises other connective tissue derived materials such as, for example, small proteoglycans such as heparan sulfate, the dermatan sulfate (chondroitin sulfate B) containing PGs known as decorin and byglycan and the KS bearing PG known as fibromodulin as well as breakdown products arising from enzymatic and free radical cleavage of the matrix proteoglycans (small and large), GAGs (ChS, HA, Heparin sulfates, KS) and proteins. In addition, the hydrolysed connective tissue products described in this invention, as well endogenous peptides and protein can undergo Maillard type reactions with ascorbic acid to form new molecular entities structurally related to lipofucsin.

Methods of Obtaining GAG-peptide Complexes and Polypeptides from Connective Tissue Autolysis In one embodiment of the invention, GAG-peptide complexes and or polypeptides are derived from connective tissue by a process of autolysis. Accordingly, the invention includes a method for recovering a GAG-peptide complex and/or a polypeptide from connective tissue wherein connective tissue particles are subjected to autolysis by incubation in an autolysis medium such that a mixture of GAG-peptide complexes and polypeptides are released from the connective tissue particles into the autolysis medium. According to one embodiment of the invention, GAG-peptide complexes are recovered from the autolysis medium and separated from the polypeptides.

As used herein the term "autolysis" refers to the digestion of cellular components by endogenous hydrolases and proteinases released from lysosomes or associated with the cell and its pericellular matrix following cell death, causing self digestion of the tissue.

A person skilled in the art will appreciate that the rate of autolysis will vary with many factors including pH, temperature, concentration, tissue type, tissue particle size and time of incubation.

As used herein the term "connective tissue" refers to tissue of or derived from cartilage, lung, skin, bone, ligament or tendon. In one embodiment the connective tissue used to obtain the connective tissue derived composition is cartilage. In one embodiment the cartilage is tracheal, articular, auricular, nasal, sternal, rib skeletal, or antler cartilage. Cartilage may be however any type of cartilage or a mixture thereof or derivative thereof.

Connective tissue may be obtained from any animal species having connective tissue such as for example human, bovine, ovine, porcine, equine, avian, cervine and piscine species. Preferably the connective tissue is bovine, ovine, porcine, cervine, shark or equine.

Connective tissue obtained from an animal source is treated and washed as required by methods known in the art to remove any adhering soft tissues. Preferably the connective tissue is reduced to a particle size. The connective tissue can be reduced to a particle size by means including, but not limited to, mincing, dicing, grinding and the like. In one example particle diameter is less than about 5 mm, preferably less than about 4 mm, more preferably less than about 3 mm. Most preferably, the particle diameter is about 0.1 mm to about 3 mm. In an alternate example the connective tissue is not reduced to a particle size.

The inventor has also now found that the residual cartilage particles derived from connective tissue by the methods described in PCT/2005/000044 and PCT/AU03/00061 are suitable for use as a starting material in a method of autolysis or limited hydrolysis (described herein below). As described in PCT/2005/000044 and PCT/AU03/00061, residual cartilage particles were removed from the media and no further use of them was made. Advantageously the inventor has now performed the methods of autolysis and limited hydrolysis as described herein using residual cartilage particles as the starting material, and analysis has confirmed that the connective tissue derived composition obtained comprises at least one GAG-peptide complex comprising two or three GAG chains.

The term "residual cartilage particles" refers to those particles which are described in PCT/AU03/00061 and PCT/2005/000044 as being left in the autolysis or hydrolysis medium. It is disclosed in PCT/AU03/00061 and PCT/2005/000044 that residual particles can be removed from the autolysis media by, for example, filtration from the autolysis media. It is also understood that residual cartilage particles can be removed from a limited hydrolysis media (for example one comprising sodium hydroxide) by filtration, or by any other suitable method.

The terms "incubation", "incubate" or "incubating" mean to contact, suspend or maintain (a chemical or biochemical system) under specific conditions in order to promote a particular reaction.

The term "buffer" refers to a compound, usually a salt, which, when dissolved in an aqueous medium, serves to maintain the free hydrogen ion concentration of the solution within a certain pH range, when hydrogen ions are added or removed from the solution. A salt or salt solution is said to have a "buffering capacity" or to buffer the solution over such a range, when it provides this function. Generally a buffer will have adequate buffering capacity over a range that is within about ±1 pH unit of its pK. The salt is preferably a monovalent or divalent salt. Preferably the monovalent salt is selected from any one or more of hydrogen, sodium, potassium, or ammonium. Preferably a divalent salt selected from any one or more of calcium, magnesium, copper, or zinc. Most preferably the salt is calcium or magnesium.

Preferably the pH is in the range of about pH 2.5 to about pH 8.5, preferably about pH 3.5 to about pH 8.0, more preferably about pH 4 to about pH 7 and most preferably about pH 4.5 to about pH 7.

The term "condition" refers to other factors which affect the rate, efficiency and amount of autolysis, such as, for example, temperature and time. In one example the temperature conditions for carrying out the step of autolysis is in the range of from about 20° C. to about 45° C., preferably about 25° C. to about 45° C., more preferably about 32° C. to about 45° C., more preferably about 32° C. to about 40° C. most preferably about 37° C.

In one embodiment, the autolysis proceeds for about 44–48 hours. In another embodiment the autolysis proceeds for about 36–44 hours. In another embodiment the autolysis proceeds for about 32–36 hours. In another embodiment the autolysis proceeds for about 28–32 hours. In another embodiment the autolysis proceeds for about 24–28 hours. In one embodiment autolysis proceeds for about 16–24. In another embodiment autolysis takes about 1 to about 16 hours. Preferably autolysis proceeds for about 16–44 hours, preferably 16–28 hours and most preferably 16–24 hours.

In one embodiment, cartilage particles of about 1–3 mm are subjected to autolysis in an aqueous medium at a pH of about 4–5 and temperature of about 32–45° C. for about 16–24 hours.

A connective tissue derived composition comprising a mixture of GAG-peptides and polypeptides can be recovered from the autolysis medium by well known methods. For example, methods of recovery include filtration to remove residual tissue particles from the autolysis media and recovery of the mixture of GAG-peptide complexes and polypeptides from the supernatant. In addition to, or alternatively, the mixture comprising GAG-peptide complexes and polypeptides is preferably neutralized by addition of an alkaline solution containing a cation. In one embodiment the neutralised mixture is thereafter freeze dried. In an alternate embodiment the neutralised mixture is kept as a liquid. Neutralization of the GAG-peptide complex alone or GAG-peptide polypeptide mixture is preferably effective to make the composition useful as a pharmaceutical and to stabilise the composition.

In yet more examples of recovering a mixture of GAG-peptide complexes and polypeptides the medium or supernatant is treated by precipitation with excess quantities of acetone, or aliphatic alcohols, such as, for example, ethanol or methanol. In addition to or alternatively, the method of recovery also comprises formation of water insoluble complexes with quaternary ammonium salts such as cetyl pyridinium, chloride. In a further embodiment the method comprises separation or selection of the GAG-peptide complex using size exclusion or ion-exchange or other forms of column chromatography or membrane filtration technology.

The present invention clearly extends to any combination of methods suitable to obtain a GAG-peptide complex and/or polypeptide for use in the present invention.

Limited Hydrolysis

An alternate method for obtaining at least one GAG-peptide complex and optionally at least one polypeptide from connective tissue comprises limited hydrolysis of a connective tissue, such as cartilage or a derivative thereof such as cartilage residual particles, comprising use of an acid, base or by the action of an exogenous proteinase. According to the present invention the extent of hydrolysis with alkalis, acids or proteolytic enzymes is controlled to obtain the desired GAG-peptide complex comprising 2 or 3 GAG-chains by terminating the hydrolysis reaction before it comes to completion. The rate (or extent) of hydrolysis of a protein or polymeric carbohydrate substrate is dependent on a number of factors including the concentration of the substrate, its physical form, the concentration of the proteinase, acid or base, the temperature of the hydrolysis medium, the presence and pH of a buffer, and the time course of the reaction.

Preferably the temperature for the method of hydrolysis is maintained at between 20° C. and 60° C. More preferably, the temperature is maintained at between 35° C. and 60° C. In one preferred embodiment the temperature is maintained for example at any one more of 37° C., 40° C., 43° C., 47° C., 50° C., 54° C. or 57° C.

The time course of the reaction is another element for controlling the limited hydrolysis reaction. Increasing the time period of the reaction provides more time for digestion of the GAG-peptide complexes and accordingly increasing the time of the reaction is expected to increase the proportion of GAG-peptide complexes and polypeptides having a smaller molecular weight in the mixture. Preferably the conditions are such that the maximum proportion of GAG-peptide complexes comprising 2 or 3 GAG-chains are obtained. Preferably, the limited hydrolysis reaction proceeds for between about 10 hours and 48 hours, more preferably between 24 hours and 44 hours. In several examples of the invention the limited hydrolysis method proceeds for any of 24 hours, 26 hours, 28 hours, 30 hours and 44 hours. In a preferred example the limited hydrolysis reaction is allowed to proceed for 24 hours.

Preferred proteinases useful in methods of the invention include for example cysteine proteinases such as papain, bromelain, ficin. Alternatively alkaline solutions such as for example hydroxides eg, sodium or potassium hydroxide are useful in a method of limited hydrolysis. In a preferred embodiment the concentration of the alkali is 0.1%–2.5% (w/v)

The pH of the conditions for limited hydrolysis is also adjustable to control the rate of hydrolysis and depends on the hydrolysis medium used. For example, if a protease is used then it is suitable to use a buffer having a pH preferably between about pH 6 and pH 7.5. In one example the pH of the buffer is pH 6 or 7.

Alternatively, where an alkaline hydrolysis medium is used in the hydrolysis method the pH of the medium in which hydrolysis proceeds is greater than pH 7, and preferably greater than pH 8. In alternate embodiments of the invention the pH is any alkaline pH.

In one example the hydrolysis medium comprises 2% NaOH (0.5 M NaOH) having a pH of about pH 13 or greater.

In one embodiment the conditions of limited hydrolysis comprise limited hydrolysis of tracheal cartilage using a medium comprising an exogenous protease bromelain maintained at 58° C. in a sodium bicarbonate buffer pH=6.0 for 24 hours. In another embodiment the conditions comprise limited hydrolysis of bovine tracheal cartilage with 0.1% aqueous sodium hydroxide at 37° C., for 30 hours.

In another embodiment the conditions comprise limited hydrolysis of bovine tracheal cartilage with 2% aqueous sodium hydroxide at 40° C., for 22 hours.

In yet another embodiment the conditions of limited hydrolysis comprises limited hydrolysis of cartilage residual particles using 1%, 1.5% or 2% sodium hydroxide maintained for 20–30 hours at 35–40° C. Preferably the sodium hydroxide concentration is 2% or 0.5M. Preferably the temperature is 35° C., 36° C., 37° C., 38° C., 39° C. or 40° C.

Following limited hydrolysis the GAG-peptide complex polypeptide mixture is preferably treated to neutralise, separate, precipitate recover or fraction the mixture, or a combination thereof as desired.

Accordingly in another embodiment, the method of limited hydrolysis of a connective tissue comprises neutralisation using conventional mineral acids or organic acids such as acetic acid, tartaric acid, glucuronic acid, lactobionic acid or ascorbic acid. Preferably the organic acid is acetic acid or ascorbic acid, most preferably ascorbic acid.

Methods of precipitation are within the scope of the invention and in one example the GAG-peptides obtained by the process of limited hydrolysis are precipitated and fractionated from the aqueous reaction solutions by stepwise addition of increasing concentrations of an aliphatic alcohol such as ethanol, or completely precipitated using a complexing agent, for example cetyl pyridinium chloride (CPC). The water insoluble CPC-GAG peptide complex so collected can then be treated for example with sodium thiocyanate to release the GAG-peptide back into solution.

Preferably, the desired GAG-peptide complex is separated from inorganic ions and fractionated according to size or charge using gel permeation chromatography, ion exchange chromatography or membrane filtration technologies.

Fractionation

As used herein the term "fractionation" refers to the separation of a mixture in successive stages, each stage removing some portion of the one of the components of the mixture.

In one embodiment the connective tissue derived composition comprising a mixture of GAG-peptide complexes and polypeptides prepared by the methods described herein are subjected to fractionation by ultrafiltration using for example synthetic membranes or tangential flow ultrafiltration (TFF) cartridges with different molecular weight cut-offs. The GAG-peptide complexes prepared by these methods contain fractions of bioactive polypeptides originally present in the mixture, the nature of which is determined by the type of membrane or cartridge used for ultrafiltration. The GAG-peptide complexes comprising 2 GAG chains have an approximate molecular weight of about 32,000 Da.

Accordingly, in one embodiment the mixture is fractionated to obtain at least one GAG-peptide complex and polypeptide with a molecular weight of greater than 30,000 Da. In one embodiment, the mixture is diafiltrated with a PLTK 30 K regenerated cellulose cartridge.

In another embodiment, the mixture is fractionated to obtain a GAG-peptide complex and polypeptide having a molecular weight of greater than 10,000 Da. In one embodiment the mixture is diafiltrated using a PTGC 10 K polyether sulfone.

Alternatively, by subjecting the dialysate from the 30,000 Da ultrafiltration through a 10,000 Da membrane GAG-peptides and polypeptides with molecular weights between 30,000 Da and 10,000 Da are obtained. In other embodiments, the mixture is fractionated to obtain GAG-peptides and polypeptides of greater than or less than 20 kDa, 15 kDa, 5 kDa, or 1 kDa.

Preferably, the compositions and methods of the present invention comprise a mixture of GAG-peptide complexes and polypeptides having a molecular weight of greater than 10,000 Da. More preferably the mixture comprises GAG-peptide complexes and polypeptides having a molecular weight of greater than about 20,000 Da, more preferably greater than about 30,000 Da, and most preferably comprise at least one GAG peptide complex of about 32,000 Da.

Separating and Recovering the Gag-peptides and Polypeptides of the Invention

In addition to or in the alternative of fractionation, the polypeptides and GAG-peptide complexes are separated by methods such as for example ion-exchange, chromatography, or precipitation.

In one embodiment, the mixture of a GAG-peptide complex and polypeptide is subjected to an ion exchange technique. In a preferred embodiment the mixture is separated by treatment with ion exchange solid phase media, such as for example DEAE sepharose, or pre-swollen DEAE-Sepharose-6B.

In alternate methods of separation, the mixture is centrifuged and the supernatant recovered. In one embodiment the supernatant is subjected to ultrafiltration, preferably using a 0.5 k Da cut-off membrane optionally in the presence of nitrogen gas to remove inorganic salts. In one embodiment, the de-salted GAG-peptide complex solution is then freeze-dried and stored at −20° C.

It is understood that the embodiments of recovery, separation and fractionation apply mutatis mutandis to methods of autolysis and hydrolysis alike, and as appropriate.

Topical Composition

The topical composition of the invention preferably comprises the connective tissue composition in an amount of between about 0.1% and about 15%, more preferably 1%, to 15%, more preferably 2.5% to 15% and most preferably about 5% to 10%.

As used herein the term "topical composition" refers to a composition which is suitable for application to the surface of a body part, or a localized area of the body. Preferably the surface of a body part comprises skin or a mucous membrane.

As used herein the term "subdermal" refers to being located or placed beneath skin or a mucous membrane. Preferably the subdermal tissue refers to a subdermal connective tissue, such as, for example, muscle, ligament, tendon, bone, or joint.

According to the present invention it has been found that application of the composition to the skin or mucous membrane of a patient provides skin and subdermal benefits.

Skin care benefits achieved following topical application of the composition preferably include those selected from treating/reducing wrinkling, sagging, dryness, irritation, inflammation, swelling, scarring, aged and/or photo-damaged skin; boosting collagen deposition in skin, enhancing tissue repair; improving skin texture, smoothness and/or firmness, or a combination thereof. These may be considered to be cosmetic skin benefits. Naturally, the amount of benefit achieved, for example the amount of reduction in the appearance of wrinkles, sagging, dryness and so forth will depend on the nature of the treatment, the condition of the skin prior to treatment and the length of treatment. Measurement of a skin care benefit can be subjective. Preferably the reduction of wrinkling, sagging, etc. of a subject's skin is a reduction compared to the condition of the skin prior to initiating treatment and is apparent to the naked eye. Other skin care benefits which may be considered therapeutic and/or cosmetic include the treatment/reduction of Rosacea, particularly of the face and neck, and dermatitis of the hands, arms and legs, or other part of the body afflicted with this painful disease. In other embodiments, the composition is useful for treating damage or trauma to the skin such as for example in the case of a burn (from a hotplate) or sunburn.

Subdermal benefits achieved for the present invention include, for example, the relief of pain and stiffness in the joints of the fingers, thumb and hands, including pain and stiffness caused by osteoarthritis, or by strain or injury. The composition has also been found to relieve pain of muscles and tendons caused by strain or injury.

Other Ingredients

The composition used according to the invention also comprises a dermatologically/cosmetically acceptable vehicle to act as a dilutant, dispersant or carrier for the actives. The vehicle may comprise materials commonly employed in skin care products such as water, liquid or solid emollients, silicone oils, emulsifiers, surfactants, solvents, humectants, thickeners, powders, propellants and the like.

The vehicle will usually form from 5% to 99.9%, preferably from 25% to 90%, more preferably 30% to 80% by weight of the composition, and can, in the absence of other cosmetic adjuncts, form the balance of the composition.

Besides the actives, other specific skin-benefit actives such as sunscreens, skin-protectant agent, skin-soothing agent, moisturizers, skin-lightening agents, skin tanning agents may also be included. The vehicle may also further include adjuncts such as anti-oxidants, perfumes, stabilizers, penetration enhancers, lubricants, anti-microbial opacifiers, preservatives, colourants and buffers. Further, the composition may also include other natural or neutraceutical products.

Accordingly, in alternate embodiments the topical composition of the present invention comprises one or more ingredients selected from the group comprising for example, talc, glycerin, octyl salicylate, diisopropyl adipate, glyceryl stearate, isopropyl palmitate, hyaluronic acid, oleyl alcohol, cetearyl alcohol, ethyl hexyl methoxycinnimate, stearic acid, cetearyl alcohol, dimethicone, triethanolamine, xanthan, imidazolidinyl urea, carbomer, tocopherol acetate, diazolidinyl urea, phenoxyethanol, carbomer iodopropynyl butylcarbamate, alpha lipoic acid, sodium hyaluronate, glucosamine HCl, allantoin, tocopherol acetate, green tea extract, shea butter, grape seed extract, aloe barbadensis leaf juice, cottonseed oil, avocado oil, grapefruit seed oil, and allantoin.

In one embodiment, the topical composition comprises 5–10% connective tissue composition, purified aqua, glycerin, octyl salicylate, diisopropyl adipate, glyceryl stearate, isopropyl palmitate, oleyl alcohol, cetearyl alcohol, stearic acid, xanthan, imidazolidinyl urea, carbomer, iodopropynyl butylcarbamate, fragrance, allantoin, and tocopherol acetate. Preferably the ingredients are not derived from crustacean or shark products. Preferably the topical composition is AHA and retinol free. In one embodiment, the composition contains sunscreen.

Product Preparation, Form, Use and Packaging

To prepare the topical composition used in the method of the present invention, the usual manner for preparing skin care products may be employed. The active components can suitably first be dissolved or dispersed in a portion of the water or another solvent or liquid to be incorporated in the composition. The preferred compositions are oil-in-water or water-in-oil or water-in-oil-in-water emulsions.

The composition may be in the form of conventional skincare products such as a cream-gel, or lotion, capsules or the like. The composition can also be in the form of a so-called "wash-off" product, e.g. a bath or shower gel, possibly containing a delivery system for the actives to promote adherence to the skin during rinsing. Most preferably the product is a "leave-on" product; that is, a product to be applied to the skin without a deliberate rinsing step soon after its application to the skin.

The composition may be packaged in any suitable manner such as in a jar, a bottle, tube, roll-ball, pump, spray or the like, in the conventional manner.

The method according to the invention may be carried out one or more times daily to the skin which requires treatment. The improvement in skin appearance will usually become visible after 3 to 6 months, preferably even after only 2–3 applications depending on skin condition, the concentration of the active components used in the 9 inventive method, the amount of composition used and the frequency with which it is applied. In general, a small quantity of the composition, for example from 0.1 to 5 ml is applied to the skin from a suitable container or applicator and spread over and/or rubbed into the skin using the hands or fingers or a suitable device. A rinsing step may optionally follow depending on whether the composition is formulated as a "leave-on" or a "rinse-off" product.

It will be understood that some cosmetic and therapeutic compositions may be made available to the general public as "over the counter" products. In a preferred embodiment of the present invention the topical composition is suitable to be made available to the general public over the counter. In an alternative embodiment of the invention the topical composition is not suitable to be made available to the general public over the counter.

EXAMPLES OF THE INVENTION

Materials and Methods

Example 1

Products isolated from cartilages by the method of autolysis according to PCT/AU03/00061 comprising a mixture of at least one GAG-peptide and at least one polypeptide are referred to herein as Peptacans. The different Peptacans isolated by the methods herein are identified by the addition of prefixes, Thus:

Calcium Peptacan (CaP)— is the aqueous soluble product obtained by subjecting bovine tracheal cartilage powder to autolysis at 37° C. with 0.1 M calcium acetate at pH 4.5.

Sodium Peptacan (NaP)— is the aqueous soluble product obtained by subjecting bovine tracheal cartilage powder to autolysis at 37° C. with 0.1 M sodium acetate at pH 4.5.

Water Peptacan ($H_2OP$)— is the aqueous soluble product obtained by subjecting bovine tracheal cartilage powder to autolysis at 37° C. with dilute acetic acid pH at 4.5.

dCaP—is CaP dialysed against $H_2O$ dNaP—is NaP dialysed against $H_2O$ dH2OP—is $H_2OP$ dialysed against $H_2O$ pCaP—is CaP purified by gel filtration or ion exchange chromatography pNaP—is NaP purified by gel filtration or ion exchange chromatography p$H_2OP$—is $H_2OP$ purified by gel filtration or ion exchange chromatography Peptacans are further described in Example 1.

1.1 Obtaining Suitable Cartilage

Bovine, ovine, cervine or porcine tracheal cartilage or nasal cartilage, chicken sternal cartilage, or skeletal shark cartilage or deer antler cartilage were freed of adhering soft tissues mechanically or otherwise. These cleaned hyaline cartilages were rinsed with water, minced into 1 mm or 3 mm sizes, freeze dried and stored at −20° C. Bovine tracheal chondroitin sulfate A (ChSA) was purchased from Sigma Chemical Co, USA or was obtained as a gift from Bioiberica, Barcelona, Spain (batch 1/0015, batch 05/2001, batch 18/11/99). All other chemicals were of analytical grade and were purchased from local suppliers.

1.2 Preparation of Glycosaminoglycan Peptide (GAG-peptide) Complexes and Polypeptides from Cartilage by Autolysis Studies on the kinetics of release of the GAG-peptides and polypeptides from the cartilage powders using the different buffers (eg sodium or calcium acetate or dilute acetic acid to give the various Peptacan products listed above in abbreviations was undertaken using a variety of conditions. The objective of these experiments was to determine the effects of (i) particle size −3 mm, 5 mm, (ii) different pHs eg. pH range 3.5–7.0, (iii) different temperatures, 4° C., 25° C. and 37° C., and (iv) animal species and tissue locations on the rate of autolysis and product release into the aqueous phase. All the experiments were performed, with stirring and release of sulphated GAGs and polypeptides monitored over 24 hours. Studies on the kinetics of release of the GAG-peptide complexes from the cartilages showed that more than 80% of the GAG content could be mobilised into the aqueous medium after 24 hours. Studies also showed that the rate of release was dependent on the cartilage particle size, the smaller preparations undergoing more rapid release. However, by 24 hours the yields obtained were the same. The pH and temperature were found to be important determinants of the rate of release which indicated that the release process was mediated by endogenous enzymes present within the solid tissues. This proposed mechanism was confirmed by undertaking autolysis experiments in the absence and presence of specific enzyme inhibitors. Since it was found that the addition of N-ethyl-maleimide produced the most significant inhibition of GAG-peptide and polypeptides release into the aqueous medium we consider that the cysteine class of proteinases, such as the Cathepsins, were the major, but not exclusive, contributors to the autolytic process.

The aqueous phase was separated from the cartilage powders by filtration and the filtrate centrifuged to remove fine particles and then neutralized to pH 7.0 by addition of an alkaline solution containing the desired cation. These Peptacan solutions after chemical analysis were either freeze dried and used directly for pharmacological studies or purified and/or converted to chondroitin sulfates. The freeze dried Peptacans were also used as stock material for the preparation of dialysed and fractionated preparations as described below. Alternatively the Peptacans could be isolated from the aqueous solutions obtained from the cartilage digests by precipitation with excess quantities of acetone, ethanol or methanol, usually by adding 3–5× the volume of the aqueous extracts. The precipitates so obtained would be washed with absolute ethanol and dried under vacuum then stored in a vacuum desiccator.

1.3 Histological Examination of Bovine Tracheal Cartilage Samples Before and after Calcium Acetate Autolysis.

Minced 3 mm cartilage samples before and after treatment with 0.1M calcium acetate, pH 4.5 at 37° C. for 24 hours were fixed in 10% (v/v) neutral buffered formalin for 48 hours. Specimens were then washed, dehydrated in increasing alcohol concentrations (70–100% v/v), and double-embedded in methyl benzoate/celloidin then paraffin wax. Sections (4 μm) were cut on a rotary microtome and adhered to Superfrost Plus (Menzel Glaser, USA) glass slides. Histochemical staining with Toluidine blue (TB), a dye which binds to sulfated GAGs and Masson trichrom (TC), a dye that binds to native collagen, was performed in batches under controlled conditions as described previously (Little C, Smith S, Ghosh P and Bellenger C R: Histomorphological and immunohistochemical evaluation of the joint changes in a model of osteoarthritis induced by lateral meniscectomy in sheep. J. Rheumatol. 24: 2199–2209, 1997). Briefly, sections were de-paraffinised, and equilibrated in 70% (v/v) alcohol for 15 minutes, then stained in 0.04% (w/v) Dye/0.1M sodium acetate buffer (pH 4.0) for 10 minutes. They were then counter-stained in 0.1% (w/v) fast green for 2 minutes, dehydrated in isopropanol followed by xylene and coverslips applied.

1.4 Purification of Glycosaminoglycan Peptide Samples by Gel Filtration

The freeze-dried Peptacans were dissolved in $H_2O$ to afford concentrations of 4.0 mg/ml of clear solutions. 1.0 ml of above Peptacan solutions was injected into a pre-equilibrated HiLoad 16/60 Superdex 200 column and eluted with 0.5 M NaCl at the flow rate of 1.0 ml/min. Fractions (2.0 ml) were collected in 5-ml plastic tubes. GAG-peptide and protein content of each fraction was determined using sulphated glycosaminoglycan (S-GAG) (Farndale R W, Buttle D J and Barrett A J. Improved quantitation and discrimination of sulfated glycosaminoglycans by use of dimethylmethylene blue. Biochim. Biophys. Acta: 883, 173–177) and BCA assay (Smith P K, Krohn R I, Hermanson G T, Mallia A K, Gartner F H, Provenzano M D, Fujimoto E K, Goeke N M, Olson B J and Klenk D C. Anal. Biochem. 150, 76–85, 1985) respectively. The fractions which were S-GAG-positive were pooled and freeze dried. These were designated as pCaP or pNaP or pH2OP.

1.5 Sulfated Glycosaminoglycan (S-GAG) DMMB Assay

The total S-GAG content of Peptacans was determined by reaction using the metachromatic dye 1,9-dimethylmethylene blue (DMMB) (Farndale R W, Buttle D J and Barrett A J. Improved quantitation and discrimination of sulfated glycosaminoglycans by use of dimethylmethylene blue. Biochim. Biophys. Acta: 883, 173–177). A standard curve was prepared using a commercially available chondroitin sulfate A (ChSA) derived from bovine tracheal cartilage (ICN, USA) in 96-well microtitre plates. ChSA standard and Peptacan samples were diluted in 0.2% sodium formate before DMMB U reagent was added and the absorbence at 535 nm read immediately. Softmax software was used to construct a standard curve and calculate the concentration of S-GAG in Peptacans.

1.6 Analysis of Cap Using High Performance Liquid Chromatography (HPLC)

The ratio of chondroitin-4-sulfate (Ch4S) and chondroitin-6-sulfate (Ch6S) isomers in Peptacans were determined using high performance liquid chromatography (HPLC) basically as described by Lee and Tieckelman (Lee G J L and Tieckelman H. The application of high performance liquid chromatography in enzymatic assays of chondroitin sulphate isomers in normal urine. J Chromatography. 222: 23–31, 1981). Freeze dried CaP was dissolved in $H_2O$ and then digested by incubation with 0.125 units of chondroitinase ABC (SKK, Tokyo Japan) at 37° C. overnight. The unsaturated disaccharides were separated in a high performance amino column using 0.2 M ammonium acetate, pH 5.5 as mobile phase and photometrically detected at 232 nm. Peaks were identified by comparison with those of chondroitin sulphate A (Sigma Chemical Co, USA). The area of each peak was measured using NIH Image 1.61.1 software.

1.7 Determination of Collagen or Collagen Peptide Content in Preparations by Assay for hydroxyproline The collagen content of cartilage powder, freeze dried Peptacans or cartilage residue after extraction was estimated by measuring the concentration of the amino acid hydroxyproline which is unique to this protein. Each freeze dried Peptacan sample was directly dissolved in $H_2O$ (10 mg/ml) and then hydrolysed in 5 N HCl at 110° C. for 24 h. The unprocessed cartilage powders or residues were papain digested for 24 h first and then centrifuged and the supernatant collected, which was then subjected to 5N HCl hydrolysis as described above. The hydrolysed sample solution was neutralised to pH 7 before dilution and analysis. The hydroxyproline concentration in these solutions was determined using the method of Stegman and Stalder (Stegman H and Stalder K. Determination of Hydroxyproline. Clin. Chim. Acta 18: 267–273, 1967) by using a L-hydroxyproline standard and measuring the absorbance at 562 nm after the addition of chloramine T and p-dimethylaminobenzaldehyde to develop the chromophore. The hydroxyproline concentration was multiplied by 7.4 to give an estimate of the collagen content.

1.8 Determination of Protein Content of Reparations by the Bicinchoninic Acid (BCA) Assay The total protein content of cartilage powder, freeze, dried Peptacans or cartilage residue after extraction was determined using BCA assay (Smith P K, Krohn R I, Hermanson G T, Mallia A K, Gartner F H, Provenzano M D, Fujimoto E K, Goeke N M, Olson B J and Klenk D C. Anal. Biochem. 150, 76–85, 1985). Cartilage powder and cartilage residue were papain-digested for 16 h and centrifuged to provide clear supernatants. Each freeze dried Peptacan was directly dissolved in $H_2O$ to provide a 2.0 mg/ml solution. 20 µl of each sample solution was added to a well of 96-well plates. Just prior to assay, 50 parts of reagent 1 (0.4% NaOH; 1.7% $Na_2CO_3$; 0.95% $NaHCO_3$; 1.0% bicinchoninic acid; 0.16% $Na_2$-tartrate) was mixed with reagent 2 (4% $CuSO_4.0.5H_2O$). 200 µl of this working reagent was added to the sample solution. After incubation at 37° C. for 60 min the absorbance $A_{562}$ was read using a Thermomax microplate reader. Bovine serum albumin (BSA) or highly purified gelatine, (Sigma Chemical Co) at 0–10 µg/well were used to: construct a standard curve.

1.9 Composite Agarose Polyacrylamide Gel Electrophoresis (CAPAGE)

Each of ChSA and Peptacan samples (CaP, pCaP or papain digested CaP) were dissolved in $H_2O$ at the concentrations of 1.0–3.0 mg/ml and then mixed 1:1 with CAPAGE sample loading buffer (20 mM. Tris-acetate, pH6.3, 1 mM $Na_2SO_4$, 60% sucrose and 0.01% bromophenol blue). 20 µl of each sample equivalent to 10 µg of GAG was loaded into wells of 2 mm thick CAPAGE gel (0.6% agarose, 1.2% acrylamide, 10 mM Tris-acetate pH 6.3 and 0.25 mM sodium sulfate) and electrophoresed in the CAPAGE running buffer (10 mM Tris-acetate pH 6.3, 0.25 mM $Na_2SO_4$) at 0.150 V for 2 h. The gel was stained in a solution of 0:02% toluidine blue in 0.1 M acetic acid for 1 h, destained in 0.5 M acetic acid for 2 h and dried on an agarose gel-bound film. The dried gel was rinsed with $H_2O$ and dried again.

1.10 Determination of Average Molecular Size of Peptacans Using Gel Filtration Chromatography A HiLoad Superdex-200 prep grade prepacked column (16 mm×60 mm) and previously characterised ChS standards were used to determine the molecular size of the various Peptacans and their digested products. The column was equilibrated with 0.25 M NaCl for at least 3 h prior to loading samples. Sephadex-G200 chromatographed bovine tracheal chondroitin sulfate fractions (CS1–CS7) prepared previously were used as molecular size standards (Melrose J and Ghosh P, Determination of the average molecular size of glycosaminoglycans by fast protein liquid chromatography. J Chromatography, 1993, 637; 91–95). 1.0 ml of standard (0.5 mg/ml) or Peptacans (CaP, $H_2OP$ and pCaP) (1.0 mg/ml) were loaded into columns and chromatographed at a flow rate of 1 ml/min using 0.25 M NaCl solution. Fractions (1.0 ml) were collected in 5-ml plastic tubes. GAG content of each fraction was determined with S-GAG assay. A standard curve was constructed using molecular mass versus distribution coefficient (Kav) of CS1–CS7.

1.11 Analysis of Proteins in Peptacans by SDS-PAGE Electrophoresis

ChSA (Sigma) and CaP were dissolved in $H_2O$ and then mixed 1:1 with 2× sample loading buffer (0.07 M Tris HCl, 1.5% SDS, 20% glycerol, 0.2M DTT and 0.1% BPB) to achieve the final concentrations of 4.0–20 mg/ml. The samples were boiled in a water bath for 5 min. 20 µl of above samples were loaded into the wells of 8–16% pre-cast Tris-glycine gel (Norvex). SeeBlue pre-stained low molecular weight range protein markers (Norvex) were loaded into wells on the left-hand side of the gel and electrophoresis was performed at 125 V for 2 h The gel was stained in Coomassie blue R250 solution (40% ethanol, 10% acetic acid and 0.2% Coomassie 11250) for 30 min. and destained in a solution containing 10% ethanol and 7.5% acetic acid for 16 h. The gel was dried in a Bio-Rad Gelair drier.

1.12 Determination of DNA in Peptacans and Commercial Chondroitin Sulfates Using UV Spectroscopy Chondroitin sulfates (Bioiberica or Sigma) and Peptacans (CaP, NaP and H2OP) were prepared at 1.0 mg/ml in H2O. 100 µl of each sample solution were loaded into a microcuvette and scanned spectrophotometrically over the wavelength range of 220–320 nm. The absorbence curves, A260 and 80 were recorded for each sample in triplicate. The absorption of light by concentrated aqueous solutions of these preparations at the wavelength of 260 nM in their UV spectra provides a measure of the levels of DNA present; whereas absorption by these solutions at 280 nM is taken as a measure of protein content. The ratio of the A 260 and A 280 values is commonly used as an index of DNA purity, with ratios of more than 1.5 being considered to indicate preparations high in DNA.

1.13 Determination of DNA in Peptacans and Commercial Chondroitin Sulfates Using the Hoechst 33258 Dye Binding Assay Chondroitin sulfates (Bioiberica or Sigma) and Peptacans (CaP, NaP and H2OP) were prepared at 1.0 mg/ml in $H_2O$ and the DNA content was determined in duplicate by using a fluorometric assay in which the Hoechst 33258 dye on binding to DNA shows a change in fluorescence (Kim Y J, Sah R L Y, Doong J-Y H, Grodzinsky A J. Fluorometric assay of DNA in cartilage explants using Hoechst 33258. Anal Biochem. 1988;174:168–176). For the cartilage preparations prior digestion with papain was employed as described by Kim et al (1988) in the in the above publication. Briefly, DNA was determined by adding 100 µl/well of Hoechst 33258 dye solution to each well of a 96-well plate followed by adding 100 µl of ChS or peptacan or papain digested samples. The plate was gently agitated for 5 min before measuring the fluorescence using excitation and emission wavelengths of 350 nm and 450 nm respectively and slit widths of 10 nm and 15 nm. Calf thymus DNA (Sigma Chemical Co)(0–25 µg/ml) with a UV spectral ratio of $A_{260}$ to $A_{280}$ of 1.85 was used to construct a standard curve and the DNA content of the preparations determined relative to this standard. DNA results were expressed as a % of the dry weight of the samples.

1.14 Determination of Binding Affinity of CaP and ChSA to Lysozyme, Elastase and Hyaluronidase Using BIAcore 2000.

The molecular interactions between CaP or ChSA and lysozyme, elastase or hyaluronidase were investigated using a surface plasmon resonance: (SPR) biosensor device—BIAcore 2000 system (Pharmacia Biosensor AB). Lysozyme (chicken egg-white, CalBiochem), elastase (human neutrophil, ICN) or hyaluronidase (bovine testes type IV, Sigma) was dissolved in 100 µg/ml in 10 mM sodium acetate, pH 6.0 and immobilized on a CM5 sensor chip by using amine coupling procedure. CaP or ChSA was firstly dissolved in $H_2O$ and then diluted in standard HBS running buffer (10 mM Hepes, pH 7.4, 150 mM NaCl, 3.4 mM EDTA, 0.005% surfactant P20) to 2.5 µg/ml. The binding of CaP or ChSA to immobilized enzymes was determined in four flow cells separately including one of the flow cells (minus ligand) used to record background sensorgrams. 200 µl of CaP or ChSA solution were injected individually on to the immobilized chip surface and the molecular interactions were monitored at the flow rate of 50 µg/ml at 25° C. The sensorgrams were recorded and evaluated using the BIAevcaluation 3.1 software provided with the system.

Example 2

2.1 Separation of Glycosaminoglycan Peptides (GAG-peptides) from Polypeptides in Peptacan Preparations by Ion-exchange Solid Phase Media GAG-peptide and polypeptide mixtures released from cartilage using different buffers (eg. sodium or calcium acetate or dilute acetic acid) according to methods described hereinabove and in PCT/AU03/00061 (referred to as peptacans) were thereafter separated. First the freeze dried peptacans were dissolved in 0.1M calcium chloride buffered with Tris-HCl to a pH of 7.2 (application buffer) to afford sample concentrations of 4.0 mg/ml. To this solution was added pre-swollen DEAE-Sepharose-6B, or a similar medium, to achieve a final concentration of the ion exchanger of 100 mg/(mL. The mixture was maintained at room temperature with gentle agitation for 16 hours in 5 mL stoppered centrifuge tubes. The tubes were then centrifuged at 1000 rpm for 5 mins and the supernatant decanted off. To the remaining pellet was added 1 mL of the application buffer and the tub gently shaken, then centrifuged again as described previously. The supernatant washings were added to the original supernatant which were then subjected to ultra diafiltration using a 0.5 kDa cut-off membrane (YC05, cellulose acetate, Millipore Australia Pty Ltd. Sydney, Australia) in a stirred cell under nitrogen gas (50 psi) to remove the inorganic salts. The de-salted GAG-peptide complex solution was then freeze-dried and stored at −20° C. The GAG-peptide complexes obtained by this method were analysed for their protein and sulfated glycosaminoglycan (S-GAG) contents using the standard methods as described herein (see Example 3). Using Calcium peptacan (CaP) as the starting material the pure GAG-peptide complex prepared by this ion-exchange procedure was identified by gel permeation chromatography and Composite Agarose Polyacrylamide Gel Electrophoresis (CAPAGE) to contain mainly 2 ChS chains attached to a short peptide stub and was annotated as GAG-P for all subsequent experiments.

Example 3

3.1 Preparation of a GAG-peptide Complex by Limited Hydrolysis (i) Preparation of non-hydrolysed tracheal cartilage proteoglycans as a chromatography standard comprised mincing freshly cleaned bovine tracheal cartilage (3 mm) and suspending 10 grams of the mince in 100 mLs of aqueous 4M guanidinium chloride (pH 5.8) at 4° C. for 48 hours as described by Inerot and Heinegard [Interot S and Heinegard D, Bovine tracheal cartilage proteoglycans. Variations in structure and composition with age. Collagen and Related Research, 3: 245–262, 1983]. The guanidinium chloride and other inorganic salts were dialysed out, the water was removed by freeze-drying and the extracted proteoglycans were obtained as a white powder.

(ii) Hydrolysis using Bromelain comprised taking one kilogram of freshly cleaned and minced bovine tracheal cartilage, and subjecting the minced cartilage to 5 L of purified water containing 10 grams of sodium bicarbonate and 5 grams of Bromelain maintained at 60° C. and a pH of 4.8. After 24 hours the mixture was neutralised, filtered and freeze dried to yield 287 grams of a white powder. The composition and molecular weight distribution of the GAG-peptide complex in this preparation was determined by the assay methods described below.

(iii) Hydrolysis using aqueous sodium hydroxide comprised suspending aliquots of freeze-dried tracheal cartilage powder (10 grams) in 100 mLs of aqueous sodium hydroxide at concentrations varying from 0.1–2.0%. The stirred suspensions were incubated at 37° C. for 4, 8, 16, 24, 26, 28, 30 or 44 hours. Mixtures were adjusted to pH 7 with either acetic acid or ascorbic acid then filtered through a bed of diatomised earth (Celite). The resulting clear solutions were then subjected to Superdex-200 gel filtration chromatography to determine the size distribution and polydispersity of the GAG-peptide fractions released by hydrolysis.

3.2 Fractional Separation of Glycosaminoglycan Peptides (GAG-peptide Complexes) by Tangental Flow Ultrafiltration (TFF)

Figure 2:
FIG. 2 provides photomicrographs of histological sections of 3 mm bovine tracheal cartilage powders particles before and after subjecting them to the autolysis procedure using 100 nM calcium acetate buffer, pH 4.5 at 37 degrees C. Panels A and C are sections of cartilage before autolytic processing and B and D after. Panels A and B show the results of staining with Toluidine Blue (TB), a dye which binds to glycosaminoglycans (GAGs) while C and D show sections stained with Masson Trichrome (Masson T C), a dye known to stain native collagen fibres magenta colour. Note the loss of staining for GAGs in section B after autolysis but a slightly increased intensity of staining for collagen following the removal of the majority of GAGs as shown in D. Cell nuclei, identified in these sections by the green counter-stains are clearly unchanged by the autolytic process. All sections are shown at magnification ×400.
Figure 2:
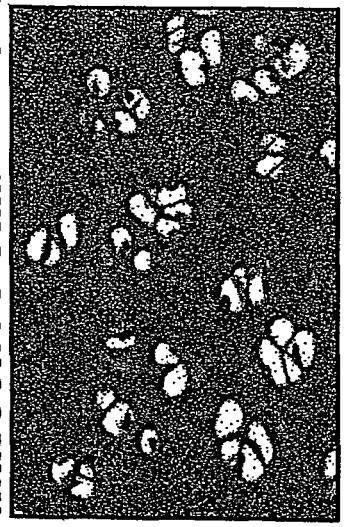
Figure 2:
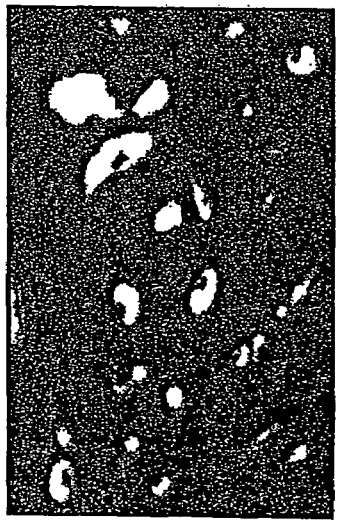
Figure 2:
Figure 3:
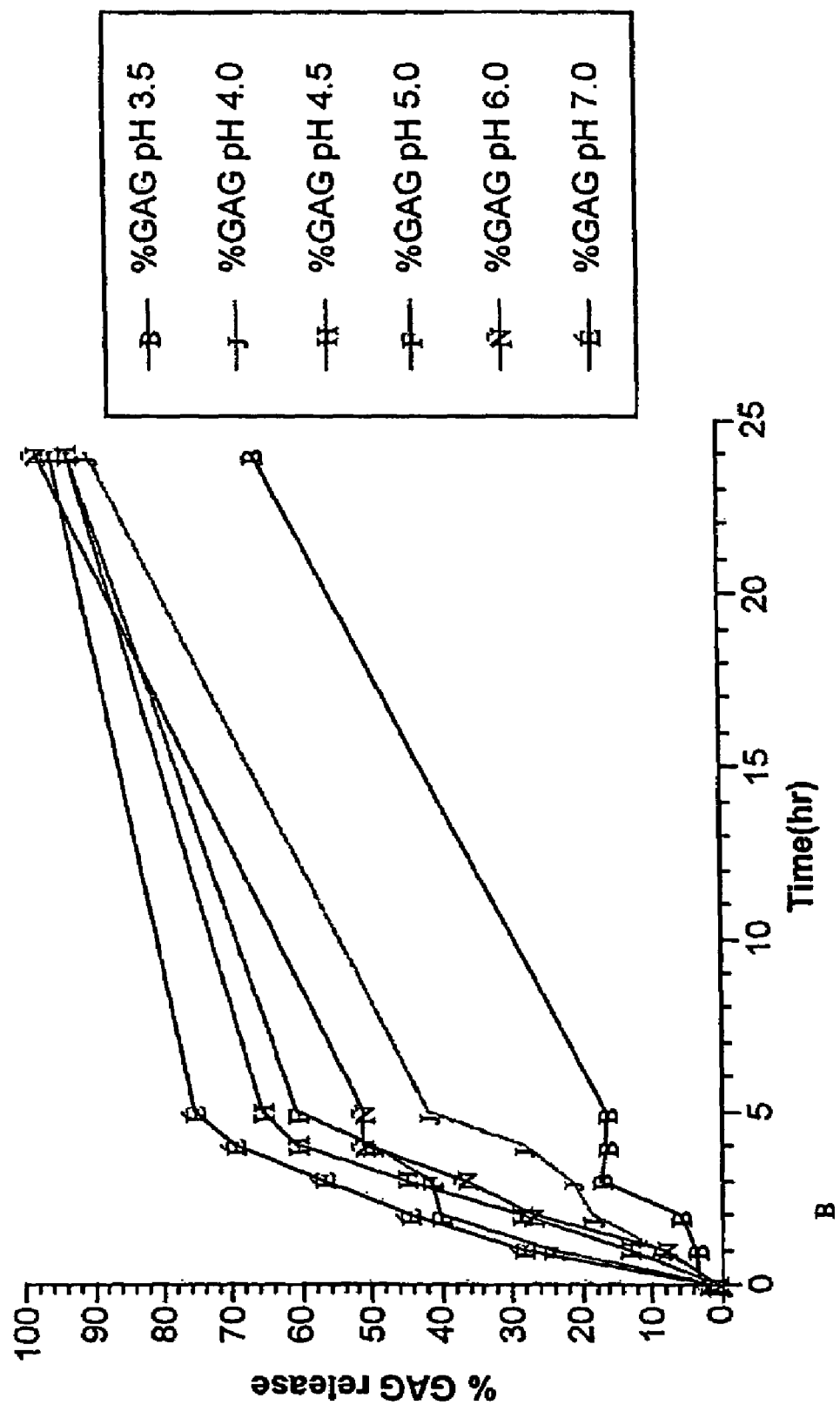
FIG. 3 provides a line graph of the kinetics of release of glycosaminoglycans-peptides (GAGs) from bovine tracheal cartilage in the presence of 100 mM calcium acetate at 37 degrees C. at various pHs.

Subjecting aqueous solutions of mixtures of GAG-peptides and polypeptides prepared by the autolysis or limited hydrolysis to partial fractionation using tangential flow ultrafiltration (TFF) with membranes of different molecular weight cut-offs afforded GAG-peptide complexes within predetermined molecular size range. For example using a PLTC regenerated cellulose membrane with an exclusion size of 30,000 afforded a mixture of GAG-peptides and polypeptides in the retentate with molecular weights greater than 30,000 Da while the dialysate contained polypeptides with molecular weights less than 30,000 Da. The redistribution of polypeptides using this method was confirmed by SDS-PAGE (FIG. 2) while the size of the GAG-peptide complexes were determined by Superdex-200 chromatography (FIG. 3). The preparation isolated from the retentate was assigned the abbreviation GAG-P30 for subsequent experiments. Likewise, TFF fractionation of autolysis of limited hydrolysis solutions using a polyethersulfone spiral cartridge with an exclusion size of 10 kD afforded a mixture in the retentate containing GAG-peptides together with polypeptides with molecular weights>10,000 Da. This preparation was assigned the abbreviation GAG-P 10 in subsequent experiments.

Calcium peptacan was also sub-fractionated using ultrafiltration membranes of other molecular weights such as membranes with cut-offs of 20 or 1 kDa, the preparations so obtained being annotated as GAG-P20 and GAG-P1 respectively. These preparations were analysed for their protein and sulphated glycosaminoglycan (S-GAG) contents and molecular weight distribution using the standard methods described below.

3.3 Analysis of Polypeptides Separated by Ion Exchange Using SDS-polyacrylamide Gel Electrophoresis (SDS-PAGE Freeze dried polypeptide samples were dissolved in $H_2O$ and then mixed 1:1 with 2× sample loading buffer (0.07 M Tris HCl, 1.5% SDS, 20% glycerol, 0.2M DTT and 0.1% BPB) to achieve the final concentrations of 4.0–20 mg/ml. The samples were boiled in a water bath for 5 min. 20 μL of above samples were loaded into the wells of 8–16% pre-cast Tris-glycine gel Norvex). SeeBlue pre-stained low molecular weight range protein markers (Norvex) were loaded into wells on the left-hand side of the gel and electrophoresis was performed at 125 V for 2 h. The gel was stained in Coomassie blue R250 solution (40% ethanol, 10% acetic acid and 0.2% Coomassie R250) for 30 min and de-stained in a solution containing 10% ethanol and 7.5% acetic acid for 16 h. The gel was stored as a digitalised electronic image then dried in a Bio-Rad Gelair drier.

3.4 Analysis of Hydrolysed Tracheal Cartilage and Gag-peptide Complexes from Membrane Diafiltration Using Superdex-200 Gel Permeation Chromatography Aliquots (0.5–1 mL) of hydrolysis solutions or CaP preparations subjected to the TFF procedure were applied to a pre-packed 34×2 cm Superdex-200 (Pharmacia, Sydney, Australia) chromatography column in 0.25M NaCl. The column was eluted with 0.25M NaCl at a flow rate of 1.0 mL/minute. Fractions (1.0 mL) were collected and assayed for the levels of sulfated glycosaminoglycans using the method of Farndale et al as described below. The column void volume (Vo) and total volume (Vt) were determined using Dextran 2000 and radioactively labelled sulfate ion respectively. The elution volume for ChS was determined for a pharmaceutical grade preparation obtained from Bioiberica Ltd, Barcelona, Spain. The exclusion volume for purified non-hydrolysed tracheal cartilage PGs was also determined using the preparation described above.

3.5 Sulfated Glycosaminoglycan (S-GAG) DMMB Assay

The total S-GAG content of samples was determined by binding to the metachromatic dye 1,9-dimethylmethylene blue (DMMB) [see the method of Farndale R W, Buttle D J and Barrett A J. Improved quantitation and discrimination of sulfated glycosaminoglycans by use of dimethylmethylene blue. Biochim. Biophys. Acta: 883, 173–177, 1986]. A standard curve was prepared using a commercially available chondroitin sulfate A (ChSA) derived from bovine tracheal cartilage (ICN USA) in 96-well microtitre plates. ChSA standard and Peptacan samples were diluted in 0.2% sodium formate before DMMB reagent was added and the absorbance at 535 nm read immediately. Softmax software was used to construct a standard curve and calculate the concentration of S-GAG in samples.

3.6 Composite Agarose Polyacrylamide Gel Electrophoresis (CAPAGE)

Standard ChSA and GAG-peptide samples prepared by the methods described herein were dissolved in $H_2O$ at the concentrations of 1.0–3.0 mg/ml and then mixed 1:1 with CAPAGE sample loading buffer (20 mM Tris-acetate, pH6.3, 1 mM Na2SO4, 60% sucrose and 0.01% bromophenol blue). Twenty micro liters of each sample, equivalent to 10 μg of GAG, was loaded into wells of 2 mm thick CAPAGE gel (0.6% agarose, 1.2% acrylamide, 10 mM Tris-acetate pH 6.3 and 0.25 mM sodium sulfate) and electrophoresed in the CAPAGE running buffer (10 mM Tris-acetate pH 6.3, 0.25 mM Na2SO4) at 150 V for 2 h. The gel was stained in a solution of 0.02% toluidine blue in 0.1 M acetic acid for 1 h, de-stained in 0.5 M acetic acid for 2 h and dried on an agarose gel-bound film. The dried gel was rinsed with $H_2O$, scanned and digitalised as an electronic image then dried in a Bio-Rad Gelair drier for storage.

3.7 Determination of the Concentration Dependent Anticoagulant Effects of CaP, GAG-peptide Complex Preparations and Commercial Chondroitin Sulfate Preparations as Assessed from the Activated Partial Thromboplastin Time (aPTT)

Pharmaceutical quality chondroitin sulfate were obtained from Bioiberica, Barcelona, Spain (ChS#1) and Sigma Chemical Co St Louis, Mo., USA (ChS#2). Calcium peptacan (CaP), and GAG-peptide (GAG-P), prepared as described herein, were evaluated for their anticoagulant activities using a commercial aPTT reagent (Actin FSL activated PTT reagent, Dade-Behring Margurg GmbH, Marburg, Germany) and a standard human plasma: (Ci-Trol Coagulation Control level 2, Dade-Behring Margurg GmbH, Marburg, Germany) according to the protocol supplied by the manufacturer. Stock solutions of the test preparations were dissolved in 0.025M calcium chloride and serially diluted in this buffer to correspond to the concentrations of 0–1.25 mg/mL. The aPTT times were determined by the addition of these solutions to a mixture of the Actin FSL reagent and control plasma held at 37° C. in cuvettes of a fibrin-timer (Dade-Behring Margurg GmbH, Marburg, Germany). This instrument quantitated the time in seconds for clot formation. All samples were assayed in duplicate and the mean values plotted against concentration using a semi-log scale.

Example 4

4.1 Preparation of Glycosaminglycan Peptide (GAG-P), INR-918R, from Cartilage Residual Particles Using Ascorbic Acid.

Figure 18:
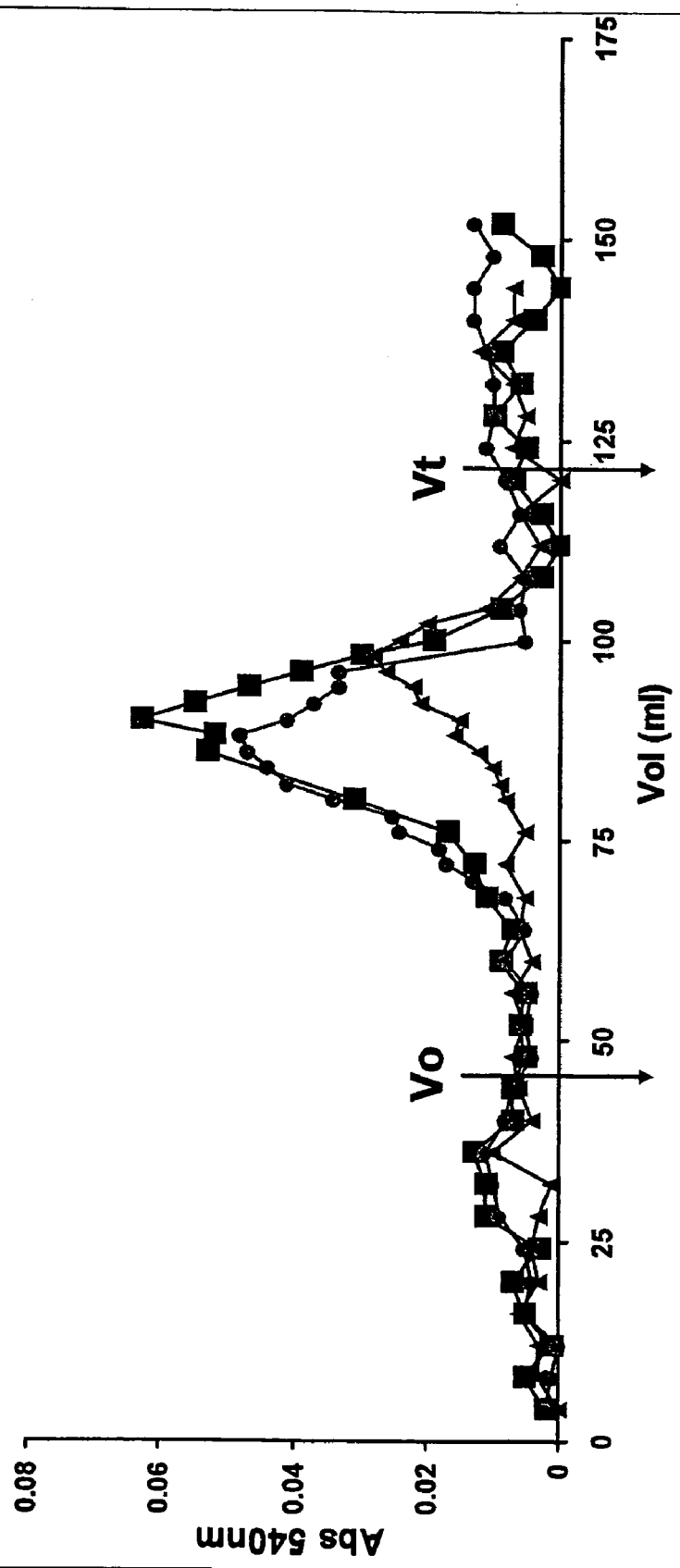
FIG. 18 provides a Superdex-200 gel permeation chromatographic (GPC) profile of glycosaminoglycan peptides isolated from hydrolysis of bovine tracheal cartilage or the residue remaining from the preparation of Calcium Peptacan as described previously. The column was eluted with 0.25M NaCl at a flow rate of 1.0 mL/minute.

An aliquot of the residue remaining from the preparation of Calcium Peptacan from bovine tracheal cartilage according to Patent PCT/AU03/00061 was thoroughly washed with cold purified water until free of any inorganic salts. The particles were suspended in water then filtered through a sinter glass funnel under vacuum and the residue pressed dry and air sucked through until all the adhering water was removed. 100 grams of this washed residue was suspended in 1 liter of 0.5M sodium hydroxide and stirred continuously for 20 hours at 37° C. The solution was then allowed to cool to ambient temperature and the pH adjusted to 7.0 by the addition of powdered ascorbic acid. To the solution was then added 1 gram of activated charcoal and the mixture filtered through a bed of diatomized earth (Celite #512) under vacuum. The clear filtrate was then subjected to rotary evaporation to remove the excess water leaving a brown, highly viscose syrup (yield 116 grams). On standing for several days at 4° C. in the refrigerator this syrup crystallised to yield a light brown solid. This material was subjected to direct biochemical analysis and also characterised by gel permeation chromatography on Superdex-200 following dialysis against purified water the fractions being monitored for sulfated glycosaminoglycans (FIG. 18) and protein (FIG. 19) using methods described herein.

4.2 Preparation of Glycosaminglycan Peptide (GAG-P), INR-919R, from Cartilage Residual Particles Using Acetic Acid.

An aliquot of the residue remaining from the preparation of calcium peptacan from bovine tracheal cartilage produced according to the method disclosed in PCT/AU03/00061 was thoroughly washed with cold distilled water until free of any inorganic salts. The particles suspended in water were then filtered through a sinter glass funnel under vacuum and the residue pressed dry and air sucked through until all the adhering water was removed. 100 grams of this washed residue was suspended in 1 liter of 0.5M sodium hydroxide and stirred continuously for 20 hours at 37° C. The solution was then allowed to cool to ambient temperature and the pH adjusted to 7.0 by the addition of glacial acetic acid. To the solution was then added 1 gram of activated charcoal and the mixture filtered through a bed of diatomized earth (Celite #512) under vacuum. The clear filtrate was then subjected to rotary evaporation to remove the excess water leaving a light brown coloured solid. This material was subjected to direct biochemical analysis and also characterised by gel permeation chromatography on Superdex-200 following dialysis against purified water the fractions being monitored for sulfated glycosaminoglycans (FIG. 18) and protein (FIG. 19) using methods described herein.

4.3 Preparation of Glycosaminglycan Peptide (GAG-P), GAG-PLH, from Bovine Tracheal Cartilage Using Ascorbic Acid (Commercial Quantity)

Finely powdered freeze dried bovine tracheal cartilage (20 kilograms) was added with continuous stirring to 200 liters of 0.5M sodium hydroxide in a stainless steel tank and then maintained at 40° C. for 22 hours. The mixture was allowed to cool to ambient temperature and the alkaline solution was adjusted to pH 7 by the addition of powdered ascorbic acid with continuous stirring. Acetic acid could also be used in place of ascorbate at this stage To the neutral solution was added activated charcoal (500 g) and diatomised earth (Celite #512) (3.0 kilograms) and the mixture then filtered under vacuum to achieve a clear brown solution. Following the addition of 250 grams of the bacterial static agent, Uniphen™, the solution was subjected to forced air evaporation of the water at 60° C. to yield a dark brown semi crystalline solid (yield 37 kilograms). Analytical characterisation of this material was undertaken using the methods described previously and below. The results obtained are provided in the results section for Example 4. Samples from this procedure were also subjected to GPC chromatography on Superdex-200 following dialysis against purified water, the fractions being monitored for sulfated glycosaminoglycans (FIG. 18) and protein (FIG. 19) using methods described herein.

4.4 Methods of Analysis of Glycosaminoglycan Peptides (Gag-P)

(i) Determination of Material Density

This assay was only undertaken on the GAG-P preparations when they were freshly prepared and obtained as viscous syrups. The volume of the syrup was determined using a Gilson viscous liquid piston pipette. Disposable plastic tips for the Gilson were accurately weighed and 1.0 mL of the syrup was aspirated separately into each of them by releasing the depressed piston. The syrup adhering to the outside of the pipette tip was carefully removed and the tips reweighed. The density of 1.0 mL of aspirated syrup was assessed as the mass of the pipette tip plus syrup minus the mass of the tip prior to filling. Each determination was undertaken in quadruplicate and the density expressed as the mean of these individual values.

(ii) Measurement of pH in Aqueous Solution

The measurement of the pH of an aqueous solution containing 10 mg/mL of the GAG-P was determined at ambient temperature using a pH meter previously calibrated against standard buffer solutions of pH 4, and pH 7. The pH of the GAG-P preparations was determined in triplicate and the results expressed as the mean values of these individual readings.

(iii) Refractive Index of Aqueous Solutions

The refractive index with reference to air is the ratio of the sine of the angle of incidence to the sine of the angle of refraction of a beam of light passing from air into the substance. The refractive index of a solution varies with the incident wavelength of the light, however, with the Abbe refractometer used for this assay the refractive indices were determined using the D band (wavelength 589.3 nm, orange colour).

Prior to examination of the GAG-P the Abbe refractometer was calibrated by placing 2 to 3 drops of distilled water onto the main prism surface with a Pasteur pipette. At a temperature of 22° C., the refractive index reading was set to 1.3330±0.0002. The water was wiped off the prism and an aqueous solution of 100 mg/mL of the GAG-P was then applied and the position of the interface between the light and dark fields was read off against the adjacent scale. In order to achieve a high degree of precision, the GAG-P solutions were measured in triplicate and the values obtained were averaged.

(iv) Transmittance of an Aqueous Solution of GAG-P at 420 nM

In this method the transmittance of an aqueous solution containing 10 mg/mL of the GAG-P was compared to a reference solution of purified water using a spectrophotometer. The spectrophotometer used was set at a wavelength of 420 nM and the reference solution was scanned first and the instrument adjusted to read 100%. This step eliminates any contributions that the solvent may make to the transmittance of light. The solvent is removed and the sample PPS solution is transferred to the same cuvette to eliminate any variability in cell construction and glass optical variation. The spectrophotometer is then read directly to provide the % transmittance of light at 420 nM for the GAG-P sample relative to the solvent blank (purified water).

(v) Total Hexosamines

In this method the total hexosamine content of the GAG-P were determined using the method of Schloss (Schloss B, Analytical Chemistry, 23:1321, 1951) after hydrolysis of the samples with 4N hydrochloric acid in a sealed glass ampules at 105° C. for 8 hours.

The levels of hexosamines released by this procedure were determined using glucosamine hydrochloride (Sigma Chemical Co) as the primary standard. Assays were performed in triplicate and the results expressed as the mean of these readings.

Example 5

5.1 Topical Anti-Inflammatory Activity of Gag-Peptide Preparations in Human Subjects (i) Erythmic Test The topical anti-inflammatory activity of the GAG-peptide preparations were evaluated in a standard chemically induced erythema test over an 8 day period. In the example presented here, a GAG-peptide preparation obtained by limited alkaline hydrolysis of bovine tracheal cartilage (GAG-PLH) was used. The GAG-PLH preparation was formulated as a 5% active in a standard cream base which contained glycerin, diisopropyl adipate, octyl salicylate, isopropyl adipate, isopropyl palmitate, stearic acid, cyclomethicone, xanthan, carbomer, allantolin, preservatives and water.

The same cream base without the GAG-PLH active was used as the placebo. The study was conducted under double blind conditions in which neither the test subject nor the assessor of the erythema score were aware of the identity of the cream applied. The subjects' left arm or right arm were randomly assigned to receive either the cream base (placebo) or the cream base plus active (active) so each subject provide his or her own control. The design of the study complied with the Helsinki criteria for experimental studies on humans and was approved by the Institutional Ethics Committee (IEC).

Before commencing the study t subjects were instructed to ref from applying any personal care or therapeutic products to the arm test area for 7 days prior to starting the investigation. Eleven subjects qualified for inclusion in the study and were enrolled but one failed to complete the final visit and was therefore excluded from the study.

Protocol

On the initial day of entry into the study the test sites on the right and left arms were wiped clean with water only. Park-Davis Readi Bandage occlusive patches (2 cm×2 cm) were impregnated with varying concentrations of sodium lauryl sulfate over the range of 0.25% to 2.0%. Similar test sites of both the inside forearms of each subject were selected and covered with a series of the prepared patches so as to elicit a graded chemically induced erythemal response. All patches were removed 22 to 26 hours after application. One hour after removal of the patches all sites were scored, using the scoring was assigned numerical values as shown below:

0=no evidence of any effect (Value=0)
?=query (Value=1)
+1=minimal, faint, uniform or spotty erythema (Value=2)
1=pink uniform erythema covering most or all of the contact site (Value=3)
2=pin-red erythema visibly uniform in entire contact site (Value=4)
3=bright red erythema with or without petechiae or papules (Value=5)
4=deep red erythema with or without vesiculation or weeping (Value=6)

Subjects were then instructed to apply either the coded placebo or the active (as defined above) undiluted creams, twice daily, morning and evening for eight days to either the erythema sites on the right or left arms. The response to treatments was assessed using the same grading system as undertaken initially as described above. Evaluation of response was then repeated at each subsequent time point i.e. 2, 4, 8 days after the initial application of the creams.

After breaking of the blinded code the individual mean responses for the 4 times points for each of the preparations was determined and compared. The Student's paired t-Test and null hypothesis were then used to evaluate the data and determine whether differences existed between the two treatment groups. $P<0.05$ was considered to be statistically significant.

5.2 Testing of Wrinkle Reduction and Skin Repair Following Topical Application

There are several methods available for the evaluation of the effects of cosmetic preparations on skin wrinkles, skin moisture and sun induced aging. In a report by Humbert P G, et al., (Topical ascorbic acid on photoaged skin. Clinical, topographical and ultrastructural evaluation: double-blind study vs placebo. Experimental Dermatology, 2003;12:237–44) the methods described measure density of skin micro-relief and wrinkle furrow depth. Humbert et al., also discloses measurement of elastic tissue repair and biomarkers used to identify sun-induced skin aging. Further practical details of how such skin characteristics can be measured is also provided by Gassmueller, J et al., in: Stylus Method for Skin Surface Contour Measurements, Handbook of Non-invasive Methods and the Skin 1995. Included below is a typical protocol and methodology for the evaluation of the ascorbate contain preparations described in this invention.

Protocol Summary

A group of female subjects is instructed to apply twice daily, in the morning and in the evening, a quantity of the test product to a designated area of the face such as the periorbital canthus (crow's foot area) around the eyes. A matched skin area (the control area) on the same subject, receives no treatment. The test subjects are instructed to use the product daily for 3 months and the designated skin areas are tested at intervals of 0, 30, 60 and 90 days post product application. Concurrent use of other moisturizers or skin care products in the target areas is excluded for the duration of the study.

Measurements

At each visit, a single silicone replica is made of the treated and control target areas on both sides of the face and a record is made of these site locations using a digital image. The silicone replica preparations are stored in controlled conditions for later profilometric measurements. Comparative skin profilometry is assessed using surface roughness analysis. This method determines the depth of the silicon replicated wrinkles as measured using a Miyomoto Surftest profilometer. Ra, Rz or Rmax values are recorded and stored electronically at each time of the measuring operation. The area scanned in from each sample is clearly mapped so as to be certain that the same area is always studied on 0, 30, 60 and 90 day after the start of the study.

Study Parameters

Washout Period for previous skin preparations: 1 week
Test Sites: Crows Feet Area
Number of Test Sites: Silicone replicas/panelist/time point (2 at each time point to be evaluated)
Number of Applications: 2 times per day.
Amount of Application: A about 0.5 ml per application
Method of application: Smooth over wrinkle and fine line area.
Number of Evaluations: 0, 30, 60 and 90 days.
Biophysical measurements: Wrinkle and Fine Line Depth Measurements.

Subject Demographics:

Preferably females between the ages of 30 and 55 years. Prior to commencement a medical history form is completed by each subject. Preferably those subjects who record a previous history of physical or dermatological conditions are excluded from the trial.

Analysis of Data

The biophysical measurements are undertaken under blinded conditions and on completion of the analysis and breaking of the code data is examined statistically using the Student's paired t-test Differences between the treated and non-treated skin area are considered to be significant when $p<0.05$.

RESULTS AND DISCUSSION

Example 1

The inventors found that subjecting cartilage particles to autolysis in aqueous buffers maintained within the pH range of 4.0–7.0, particularly 4.5, at 37° C. for periods up to 36 hours, particularly 16 or 24 hours specifically released GAG-peptide complexes and matrix derived polypeptides into solution while leaving the tissue cells and their intracellular macromolecular components essentially in tact. DNA was used as a marker for intracellular macromolecular components and demonstrated that the autolysis medium obtained by the present invention was substantially free of DNA. Moreover, these GAG-peptide complexes released into the autolysis medium, defined arbitrarily as Peptacans when used alone or in combination with other co-released polypeptides are pharmacologically more active than commercially available ChS.

Figure 1:
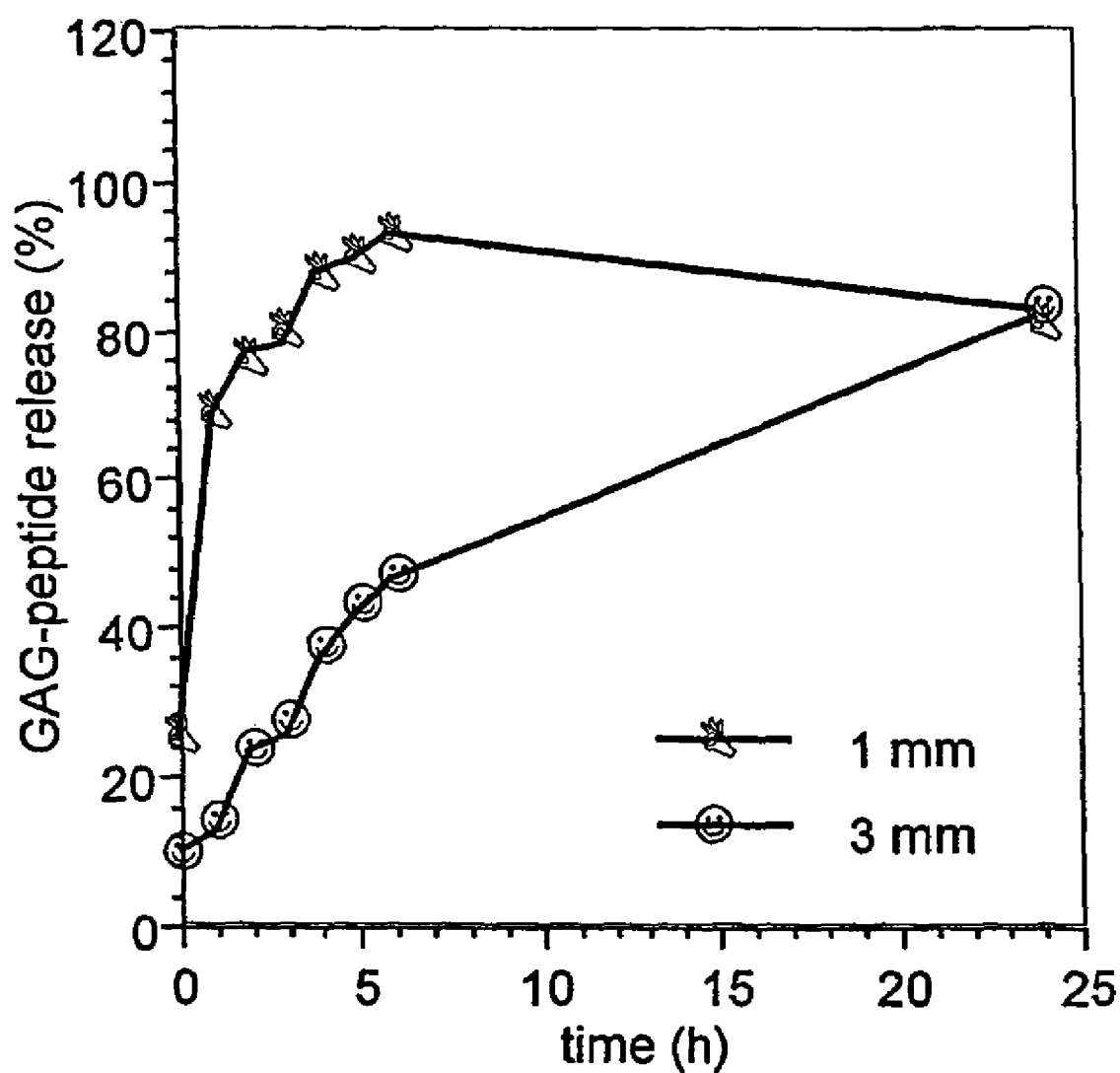
FIG. 1 provides a line graph of the kinetics of Glycosaminglycan-peptide (GAG-peptide) released from 1 mm and 3 mm bovine trachea cartilage powders with autolysis buffer, 100 mM calcium acetate, pH 4.5 at 37 degrees C.

The release of these cartilage products was found to be more rapid with smaller particles than larger ones (FIG. 1). However, when either cartilage was incubated at 37° C. over a 24 hour period 75–83% of the total tissue sulfated GAGs was released into solution as shown by analysis for this component irrespective of the particle size (FIG. 1).

The efficiency and selectivity of this method was also confirmed by histochemical analysis of the cartilage particles before and after subjecting them to the inventive method. FIG. 2 shows photomicrographs of histological sections of 3 mm bovine tracheal cartilage powders particles before and after subjecting them to the autolysis procedure using 100 mM calcium acetate buffer, pH 4.5 at 37 degrees C. Panels A and C are sections of cartilage before autolytic processing and B and D after. Panels A and B show the results of staining with Toluidine Blue (TB), a dye which binds to glycosaminoglycans (GAGs) while C and D show sections stained with Masson Trichrome (Masson T C), a dye known to stain native collagen fibres magenta colour. Note the loss of staining for GAGs in section B after autolysis but a slightly increased intensity of staining for collagen following the removal of the majority of GAGs as shown in D. Cell nuclei, identified in these sections by the green counter-stains are clearly unchanged by the autolytic process. AU sections are shown at magnification ×400.

As is evident from FIG. 2 the level of staining for the presence of sulfated GAGs in cartilage particles using the cationic stain for these molecules, Toluidine Blue, before processing was extensive but after incubation was diminished. On the other hand, Masson Trichrome staining of native collagen fibres was essentially unchanged by the autolytic process (FIG. 2). Significantly, the cells and importantly their nuclei which were clearly visible using both staining procedures of the residual cartilage, remaining after removing the supernatant and washing with the incubation buffer, were observed to be largely undisturbed FIG. 2).

Figure 4:
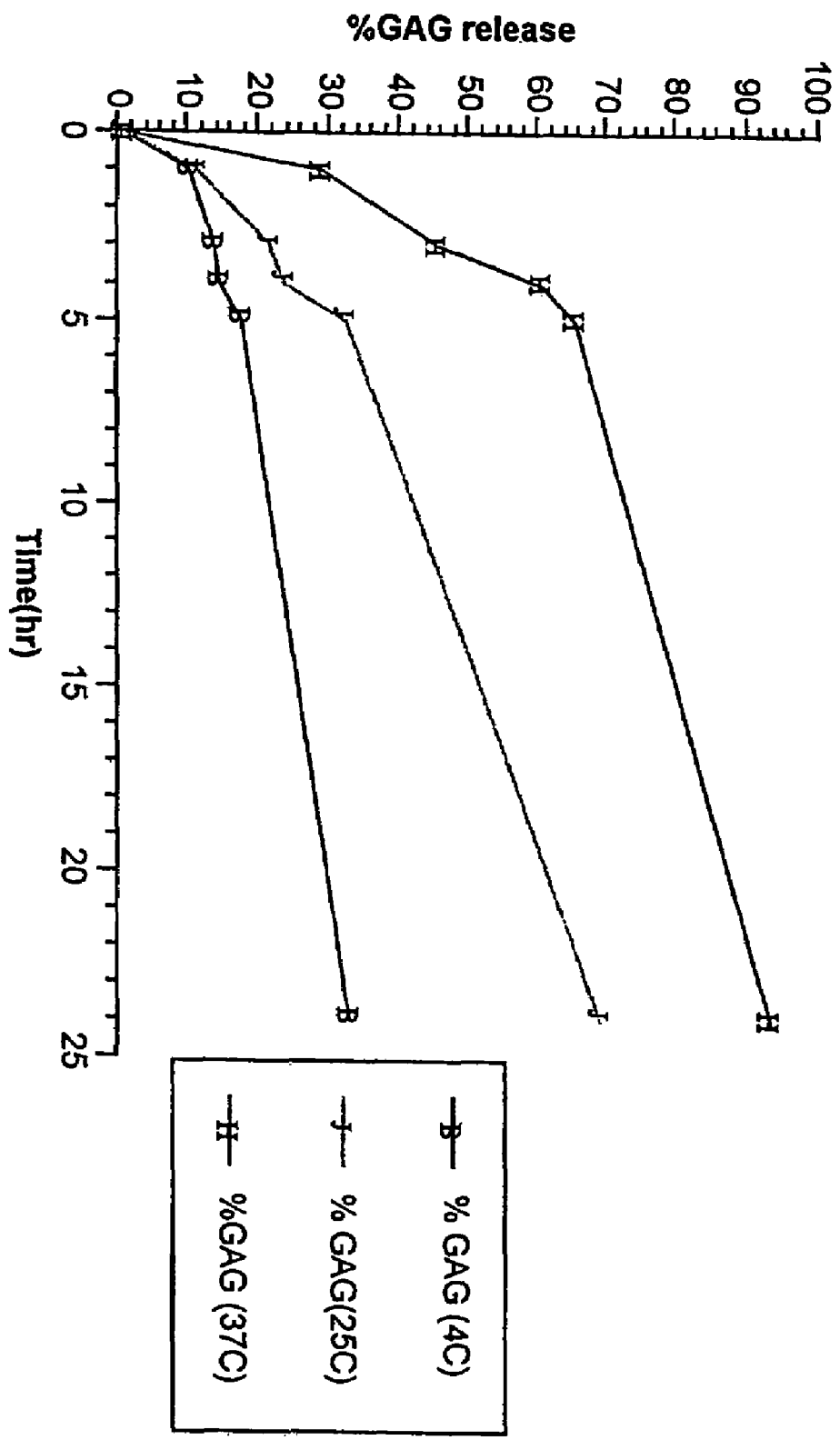
FIG. 4 provides a line graph of the kinetics of release of glycosaminoglycans-peptides (GAGs) from bovine tracheal cartilage in the presence of 100 mM calcium acetate at pH 4.5 C at various temperatures.
Figure 5:
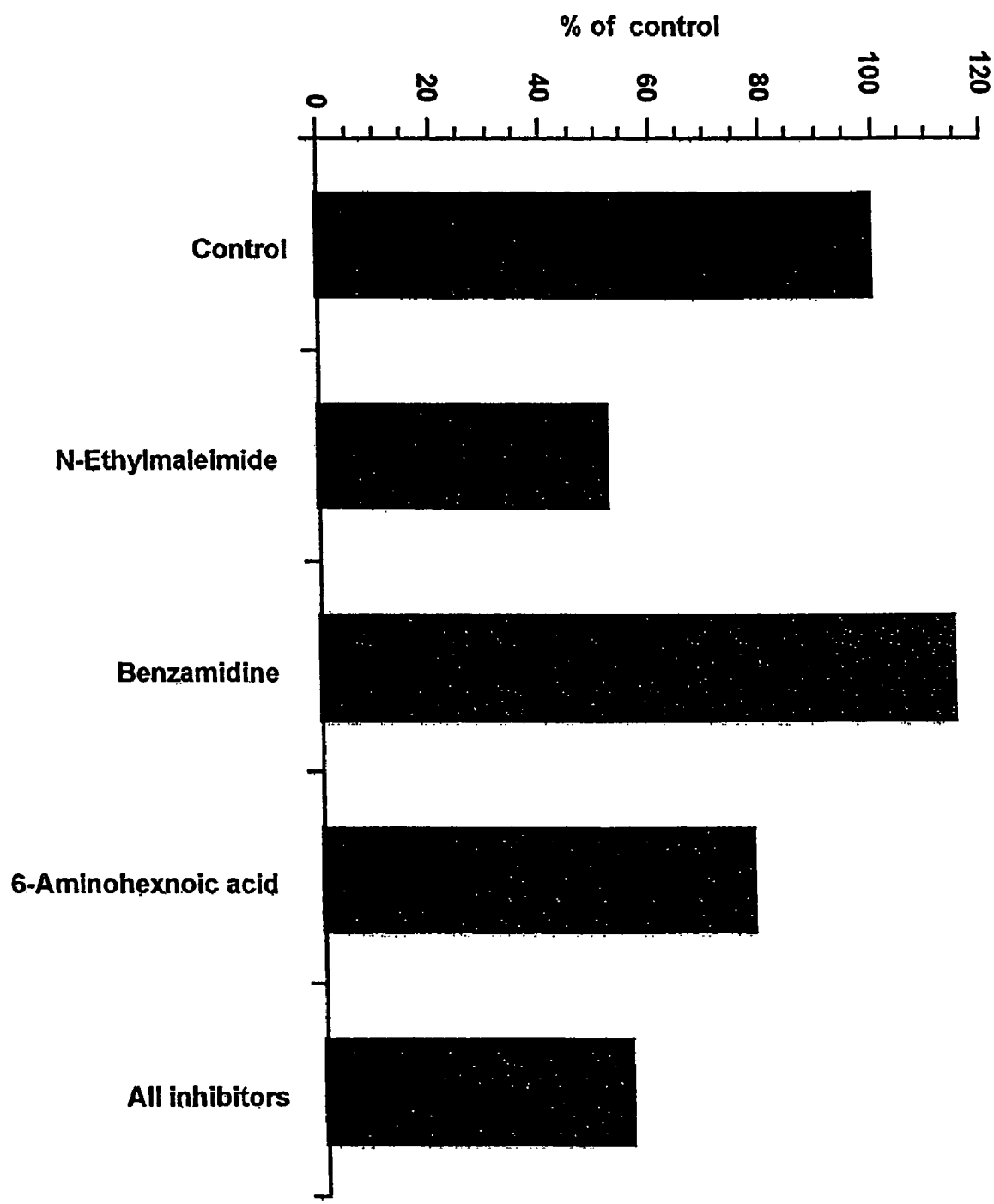
FIG. 5 provides a bar graph of the results of release of glycosaminoglycans-peptides (GAGs) from bovine tracheal cartilage in 100 mM calcium acetate buffer at pH 4.5 C at 37 degrees C. in the absence and presence of proteolytic inhibitors. The cysteine protease inhibitor, N-Ethylmaleimide was the most effective inhibitor reducing release by approximately 50% that of the control incubations which contained no inhibitors.

The autolytic process was affected by both pH and temperature. As is evident from FIG. 3 the most rapid release of peptacans from bovine tracheal cartilage occurred within the pH range 4.0–7.0. The normal mammalian blood temperature of 37 degrees C. was found to be more effective than lower temperatures, most notably 4° C. in facilitating peptacan release while intermediate levels of release occurred at 25 degrees C. (FIG. 4). The influence on this release process of both temperature and pH was consistent with the notion that autolysis was proceeding via the cleavage of matrix proteoglycans and other structural proteins by endogenous enzymes whose catalytic activities were optimum within the pH range 4.0–7.0 at 37 degrees C. This explanation was confirmed by the observation that the release process was substantially slowed by maintaining the cartilages particles in the autolysis buffers at 4° C. as well as the observation that the rate of release was markedly reduced by including specific inhibitors of proteinases in the incubations in buffers at 37 degrees C. (FIG. 5). As is evident from FIG. 5, approximately 50% inhibition of the autolytic process was achieved by the addition of the cysteine proteinase inhibitor, N-ethylmaleimide to the buffer solution. Since the major cysteine proteinases of cartilage are the Cathepsins which have pH optima between 3.5–6.0, it is most likely that these enzymes are largely responsible for the autolytic degradation of matrix components in this invention. However, as matrix component degradation was not completely abrogated by N-ethylmaleimide, other classes of proteinases are clearly involved. Since the serine proteinase inhibitor, Benzamidine had no observable effect on release, this class of proteinases would seem to be excluded.

The efficiency of the autolytic process in the present invention was also influenced by the animal species and anatomical location from where the cartilage was derived. As is evident from TABLE 1 below, bovine tracheal and nasal cartilages afforded the highest yields of peptacans when incubated at 37° C. over 24 hours. However, deer antler cartilages and avian (chicken) sterna provided more than 60% yield of peptacans under the same conditions. Surprisingly, commercially available samples of shark cartilage, of unknown location or method of preparation afforded very low yields of peptacans. Nevertheless, it is clear from these examples that the method of the invention is applicable to a wide range of connective tissues but the efficiency of release of peptacans into the aqueous medium is related to their ultrastructural assembly and means of preparation prior to autolytic treatment.

Figure 9:
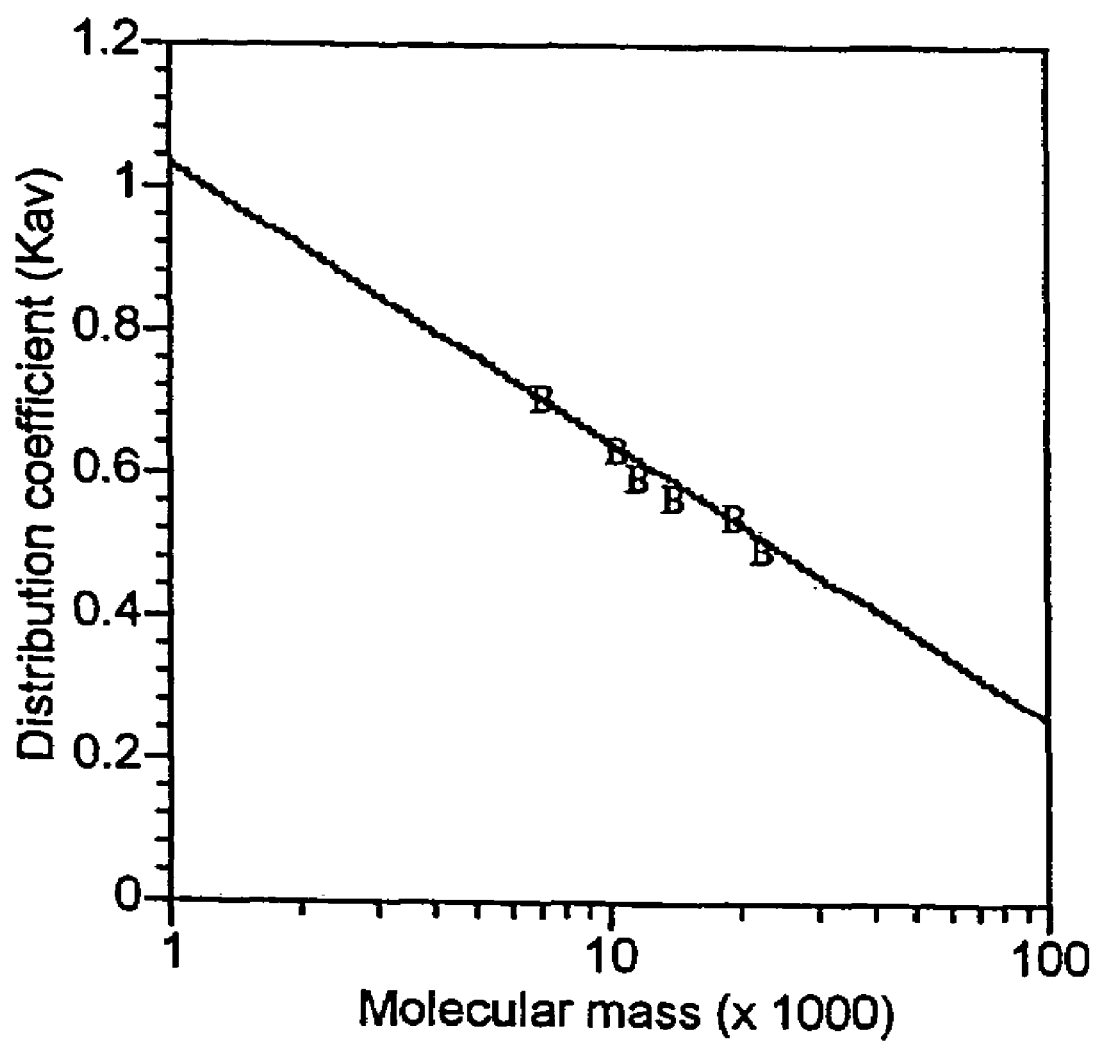
FIG. 9 provides a standard curve of distribution coefficient (Kav) versus molecular mass of ChS standards determined on Sephadex-G 200 using the method of Melrose and Ghosh (1993) as described in the text.

Chromatography, 1993, 637; 91–95). The correlation between MW and Kav obtained using these ChS standards and the Sephadex column is shown in FIG. 9 and the results obtained for the unknown preparations is shown in TABLE 2 below. These experiments confirmed that the GAG-peptide in CaP contained 2 ChS chains while that in H2OP consisted of 3 ChS chains.

TABLE 2

Average Molecular Size (KDa) of commercial chondroitin sulfates and Peptacans as determined by Gel Chromatography and standards

| | |
|---|---|
| ChSA (Sigma) | 17.3 |
| ChSA (Bioiberica) | 20.0 |
| CaP | 33.7 |
| pCaP | 31.1 |
| H2OP | 46.1 |
| MgP | 32.3 |
| ZnP | 50.4 |

TABLE 1

Kinetics of sulfated glycosaminoglycan (GAG) release from cartilages of various origins over 24 hours using 100 mM Calcium Acetate buffer pH 4.5.

| Time | % GAG released | | | | | | | |
|---|---|---|---|---|---|---|---|---|
| (hr) | (B-Tracheal) | (A-Sternea) | (B-Nasal) | (Shark) | (O-Articular) | (O-Meniscus) | (C-Antler-tip) | (C-Antler-mid) |
| 0 | 0.54 | 2.91 | 0.08 | 6.67 | 1.13 | 0.00 | 0.05 | 0.00 |
| 1 | 13.26 | 41.55 | 10.64 | 30.50 | 3.38 | 0.00 | 13.10 | 5.18 |
| 2 | 28.96 | 41.97 | 28.86 | 30.73 | 7.22 | 0.00 | 27.90 | 19.42 |
| 3 | 45.36 | 46.26 | 42.09 | 27.28 | 13.96 | 0.06 | 58.09 | 42.40 |
| 4 | 60.75 | 48.75 | 50.51 | 24.95 | 17.97 | 0.10 | 66.06 | 56.63 |
| 5 | 65.61 | 45.71 | 52.14 | 24.95 | 18.57 | 0.38 | 62.64 | 56.45 |
| 24 | 93.16 | 60.90 | 81.36 | 23.65 | 51.03 | 0.52 | 83.14 | 56.31 |

B = Bovine,
A = Avian,
O = Ovine,
C = Cervine,
Antler-mid = cartilage between tip and bone,
Shark = unknown site.

Figure 6:
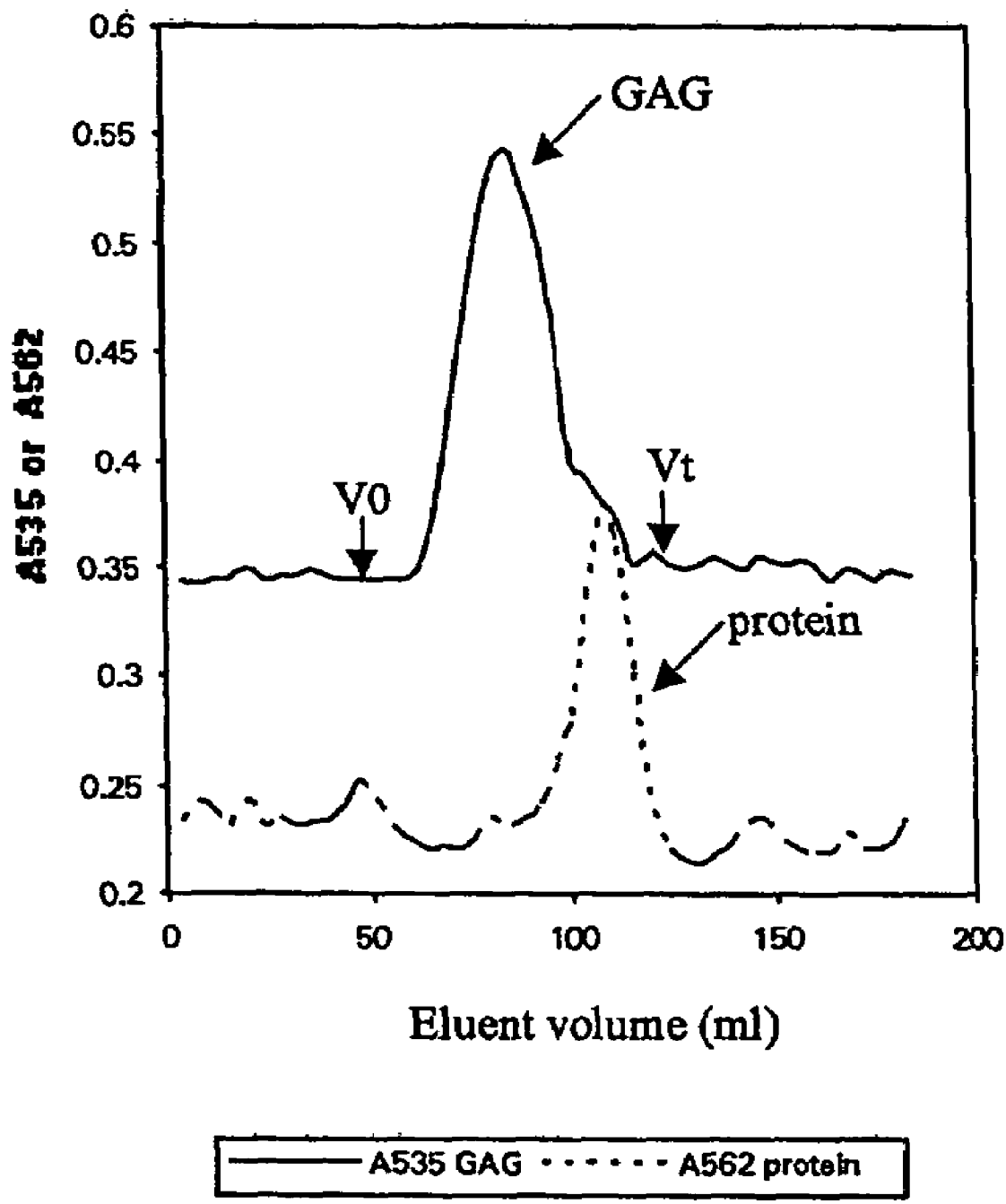
FIG. 6 provides an elution profile: Superdex-200 gel filtration of calcium peptacan (CaP) showing sulfated GAG ($A_{535}$) and protein($A_{562}$) profiles.
Figure 7:
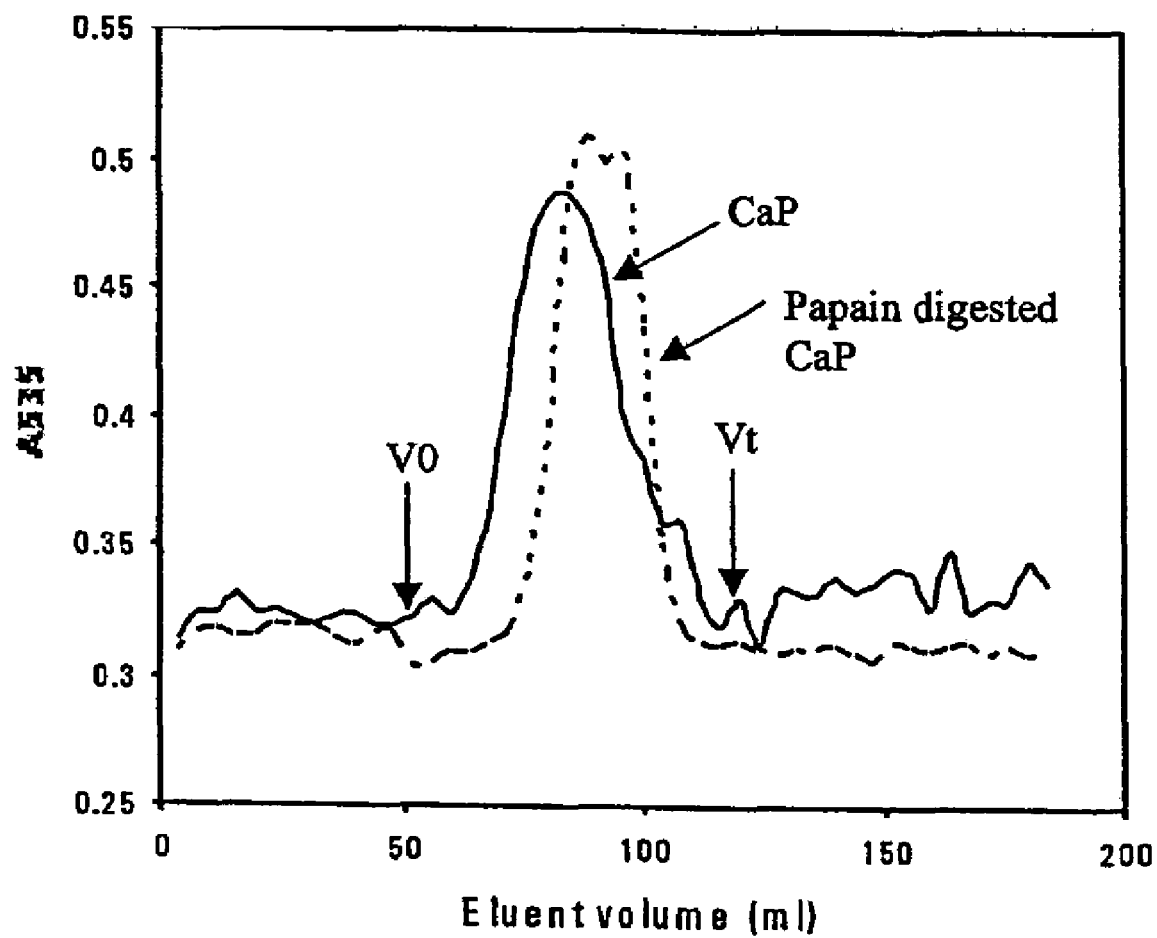
FIG. 7 provides an elution profile: Superdex-200 gel filtration profiles of calcium peptacan (CaP) and papain digested CaP showing decrease in molecular size to that of chondroitin sulfate.
Figure 8:
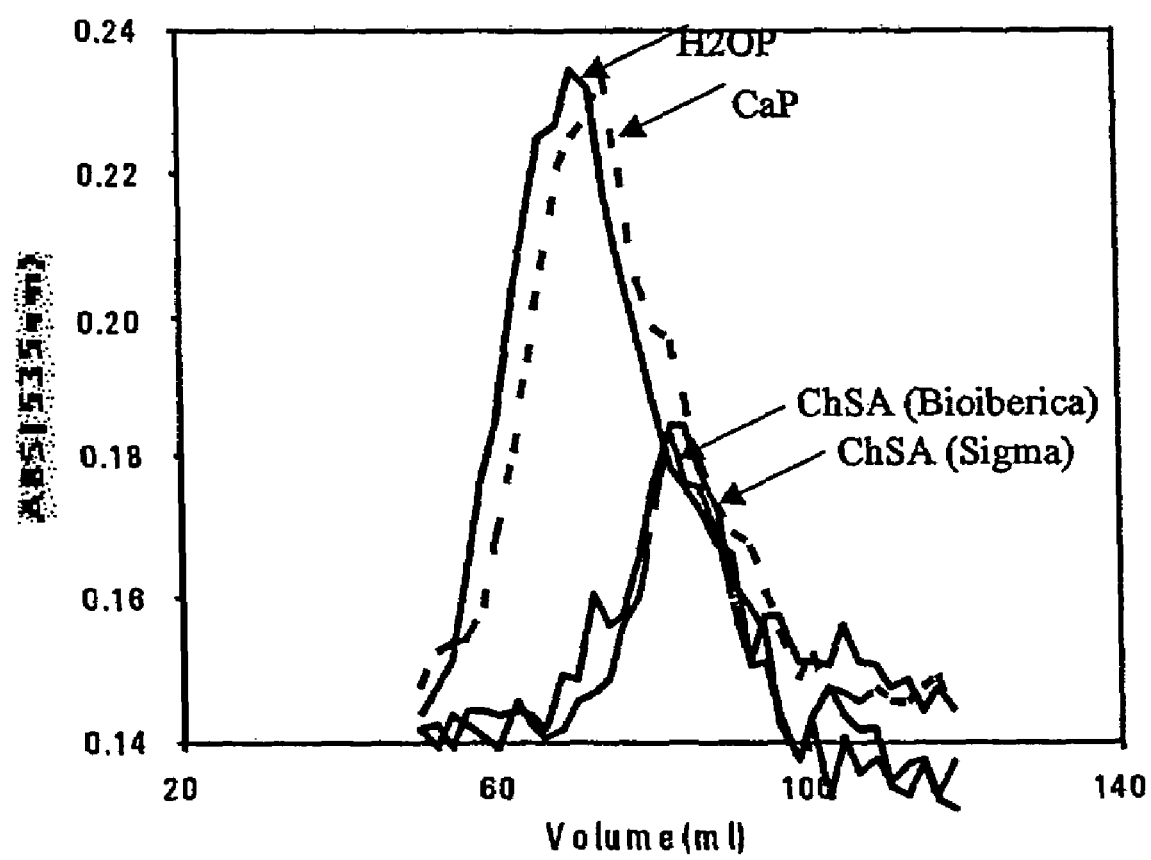
FIG. 8 provides an elution profile: Superdex-200 gel filtration chromatograms of Peptacans (CaP and H2OP) and chondroitin sulfate (ChS) (Sigma and Bioiberica).
Figure 10:
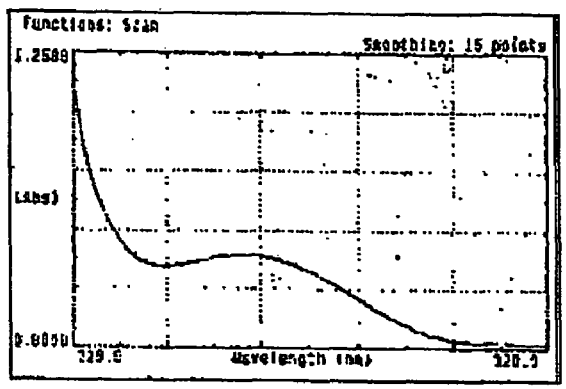
FIG. 10 provides the UV spectra of commercial chondroitin sulfate (ChSA) and Peptacans of different types. The presence of DNA is indicated by absorption at $A_{260}$ and protein at $A_{280}$. Note the low DNA absorption for the Peptacans relative to the ChSA.
Figure 10:
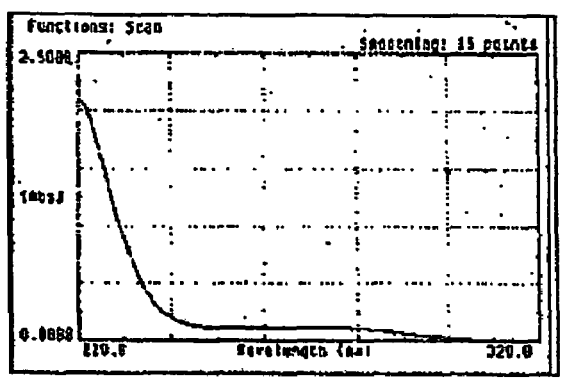
Figure 10:
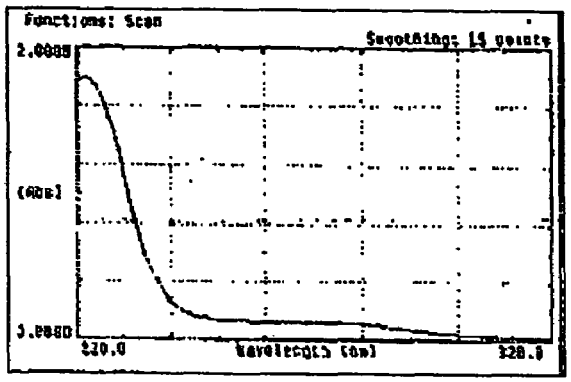
Figure 10:
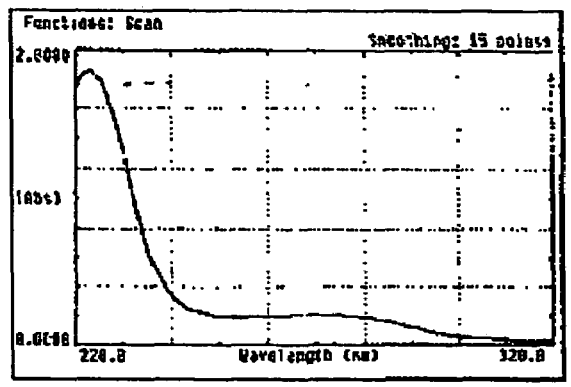
Figure 11:
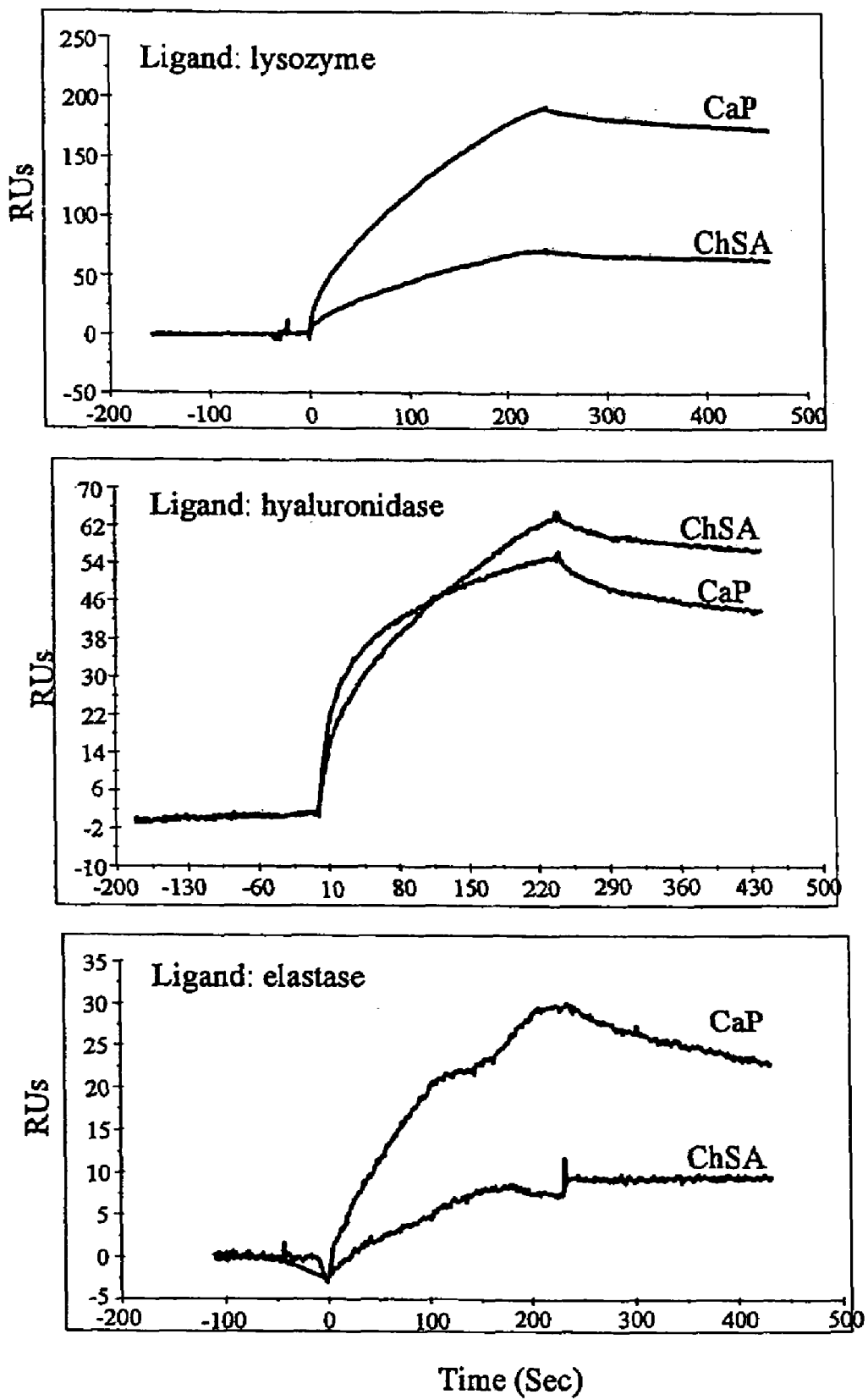
FIG. 11 provides resonance units profiles of Chondroitin Sulfate (ChS) and calcium peptacan. The resonance units represent the binding and release of ChS and Calcium Peptacan (CaP) from immobilized lysozyme, hyaluronadase, and human granulocyte elastase using the BIAcore2000 technique.

When the supernatants derived from the tracheal cartilage incubated with 0.1M Calcium Acetate were applied to a Superdex gel filtration column and fractions monitored for sulfated-GAGs and protein two resolved peaks corresponding to the GAG-peptide and polypeptides were obtained (FIG. 6). Evidence that the GAG-peptide was not simply ChS but contained more than one sulfated GAG chain was provided by its digestion with the proteolytic enzyme papain which shifted the DMMB positive peak to the same column fractions obtained when pure ChS was chromatographed under the same conditions (FIG. 7). When the supernatants obtained from incubation of 0.1M Calcium acetate pH 4.5 (CaP) and dilute acetic acid pH 4.5 (H2OP) were chromatographed under the same conditions on the Superdex-200 column it was observed that the GAG-peptide obtained with the Calcium Acetate buffer was of smaller molecular size than that released by the acetic acid digestions. Both were, however larger than two commercially available ChSs (FIG. 8). The weight average molecular masses of the CaP, H2OP, purified CaP (pCaP) and the two commercially available ChSs were then assessed using a Sephadex-G 200 high resolution gel exclusion column and seven ChS standards prepared and characterised previously (Melrose J and Ghosh P, Determination of the average molecular size of glycosaminoglycans by fast protein liquid chromatography. J Electrophoresis (Composite agarose polyacrylamide gel) of CaP, pCaP and papain digested CaP indicated that the only sulfated GAG present was ChS (FIG. 10). However, SDS-PAGE showed that CaP also contained a number of peptides with MWs of 21 KDa or less which were not present in the purified CaP.

Analysis for total protein and hydroxy proline content as a marker of collagen in these samples suggested that the dominant polypeptides released were largely derived from cleavage of collagen chains.

TABLE 3

Analysis of Peptacans and Commercial Chondroitin Sulfates For Sulfated Glycosaminoglycans, Protein and DNA content

| Samples | S-GAG (DMMB) % | Protein (BCA) % | DNA (Hoechst) % |
|---|---|---|---|
| ChSA (Sigma) | 98.5 | 0.16[a] | 0.36 |
| ChSA (Bb 1/0015,05/2001) | 97.4 | 1.25[a] | 0.32 |
| ChSA (Bb 18/11/99) | 98.1 | 0.63[a] | 0.35 |
| ChSA (NaP) | 97.8 | 0.74[a] | UN |
| ChSA (CaP) | 96.5 | 1.40[a] | UN |
| CaP | 39.8 | 35.12[b] | UN |

TABLE 3-continued

Analysis of Peptacans and Commercial Chondroitin Sulfates
For Sulfated Glycosaminoglycans, Protein and DNA content

| Samples | S-GAG (DMMB) % | Protein (BCA) % | DNA (Hoechst) % |
|---|---|---|---|
| pCaP (EtOH ppt) | 49.0 | 40.51[b] | UN |
| H2OP | 65.6 | 44.48[b] | UN |
| NaP | 53.3 | 32.93[b] | UN |
| pH2OP (column) | 85.0 | 9.60[b] | UN |
| pCaP (column) | 44.8 | 6.52[b] | UN |
| MgP | 32.5 | 36.59[b] | UN |
| ZnP | 18.6 | 38.17[b] | UN |

Figure 13:
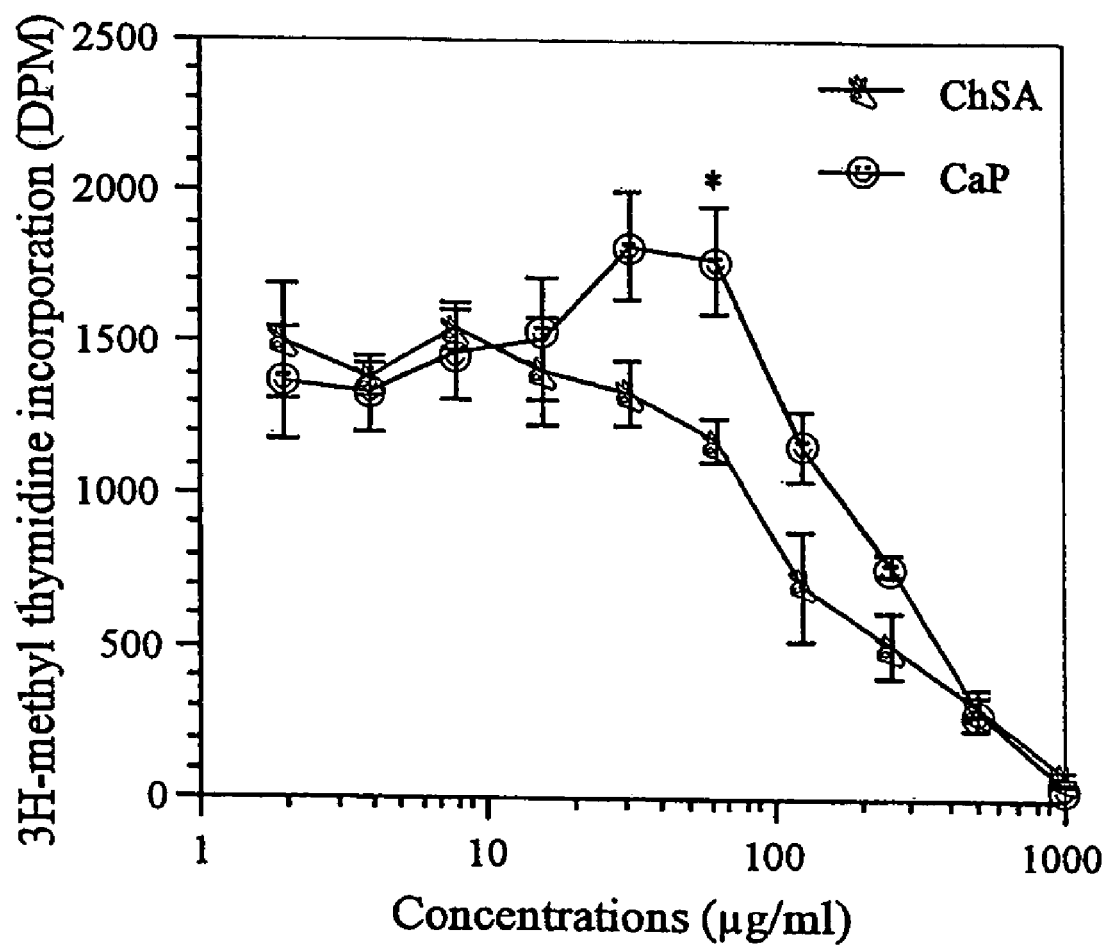
FIG. 13 provides a line graph of long-term (7 days) concentration-dependent effects of chondroitin sulfate (ChSA) and calcium peptacan (CaP) on the incorporation of $^3$H-methyl thymidine into DNA of ovine articular chondrocytes in monolayer cultures.

S-GAGs = sulfated glycosaminoglycans (method of assay used, see text)
UN = undetectable,
[a]using BSA as standard,
[b]using Gelatin as standard Spectroscopic analysis of concentrated aqueous solutions (1.0 mg/ml) of the Peptacans (CaP, NaP, H2OP) and commercial ChSs (FIG. 10) and ChSs derived from Peptacans revealed low absorption for protein at 280 nM and DNA at 260 nM for the Peptacans and the ChSs derived from them. In contrast high values for DNA were evident in the commercial ChS preparations as indicated by the ratios of A260/A280 in their uv spectra which were in the order of 1.85 or more (FIG. 10). Using a published fluorescent dye binding assay for DNA in the same samples and calf thymus DNA as a standard confirmed that the Peptacan preparations and the ChSs derived from them were substantially free of DNA, whereas the pharmaceutical quality commercial ChS examined contained approximately 0.3% DNA (TABLE 3). Analysis of the relative binding of CaP and ChS to the enzymes, lysozyme, hyaluronidase and human neutrophil elastase which are mediators of matrix destruction in arthritis using the BIAcore 2000 system showed that CaP interacted more strongly with lysozyme and elastase than ChS but with hyaluronidase there was little difference between the two preparations (FIG. 13). The higher binding affinity of CaP for the proteolytic enzyme, elastase derived from human neutrophils was confirmed using a conventional functional assay and the synthetic elastase substrate, succinyl-alanine-alanine-valine-nitroanilide (SAAVN). Using this assay system the concentration range of ChS which produced 50% inhibition of elastase (IC50) was found to be 4–5 micrograms/ml while the IC50 for the CaP preparation was between 1–3 micrograms/ml.

Figure 12:
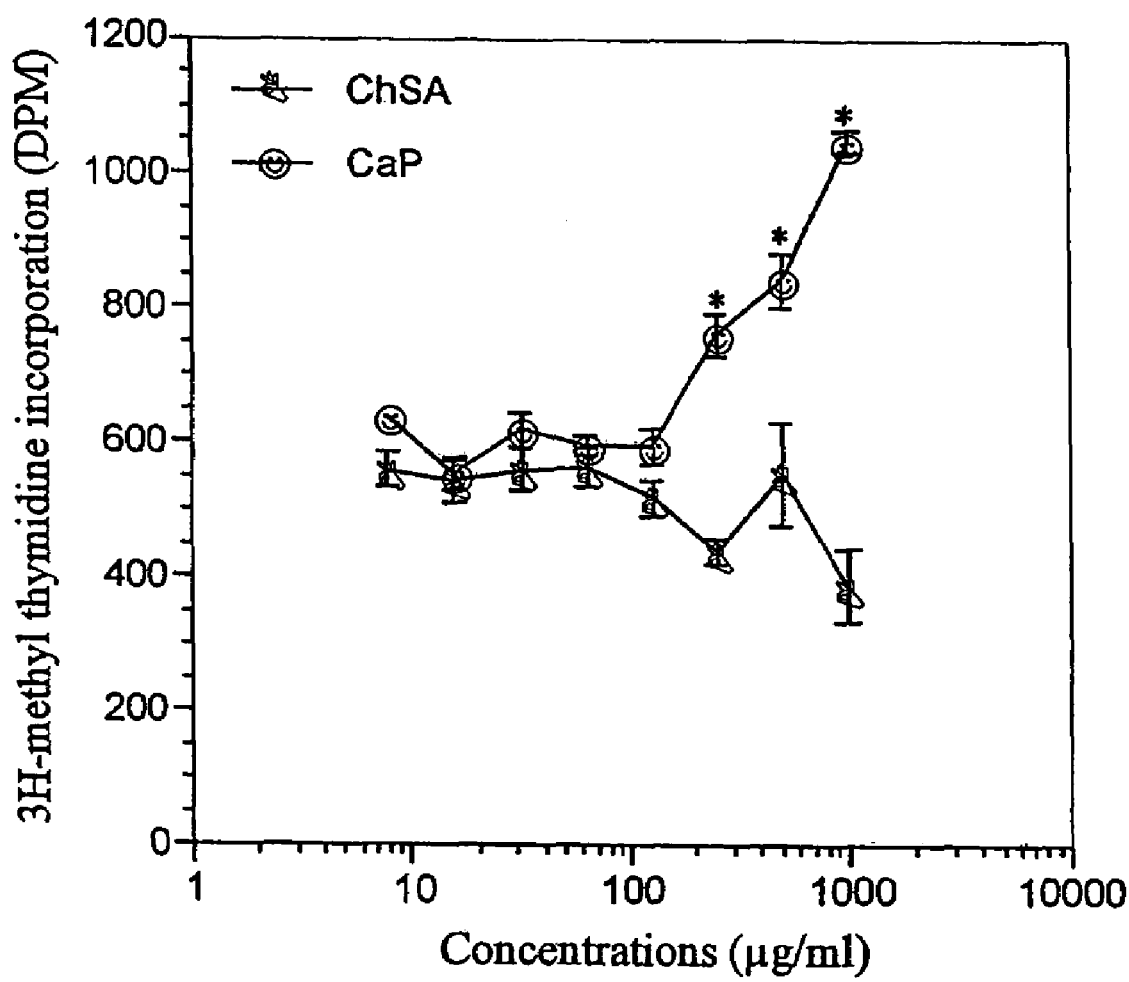
FIG. 12 provides a line graph of Short-Term (2 days) Concentration-Dependent Effects of Chondroitin Sulfate A (ChSA) and Calcium Peptacan (CaP) on the Incorporation of $^3$H-methyl Thymidine into DNA of Ovine Chondrocytes in Monolayer Cultures.

In the short term (2 days) chondrocyte cultures CaP at concentrations of 250 micrograms/ml and above stimulated cell division as indicated by tritiated thymidine incorporation into DNA while ChS had no effect (FIG. 12). In the longer term chondrocyte cultures (7 days) CaP at 62.5 micrograms/ml stimulated DNA synthesis (FIG. 13). These data clearly identify the anabolic effects of the CaP which would support the repair and regeneration of connective tissues.

As already indicated Proteoglycan are essential components of the cartilage extracellular matrix and are responsible for its unique biomechanical properties. Since these molecules are degraded and depleted from cartilage in arthritic joints, agents which can prevent this event or stimulate their biosynthesis by chondrocytes and other cells would be beneficial to the recovery of joint function and a reduction in patient symptoms.

Examples 2 and 3

Figure 14:
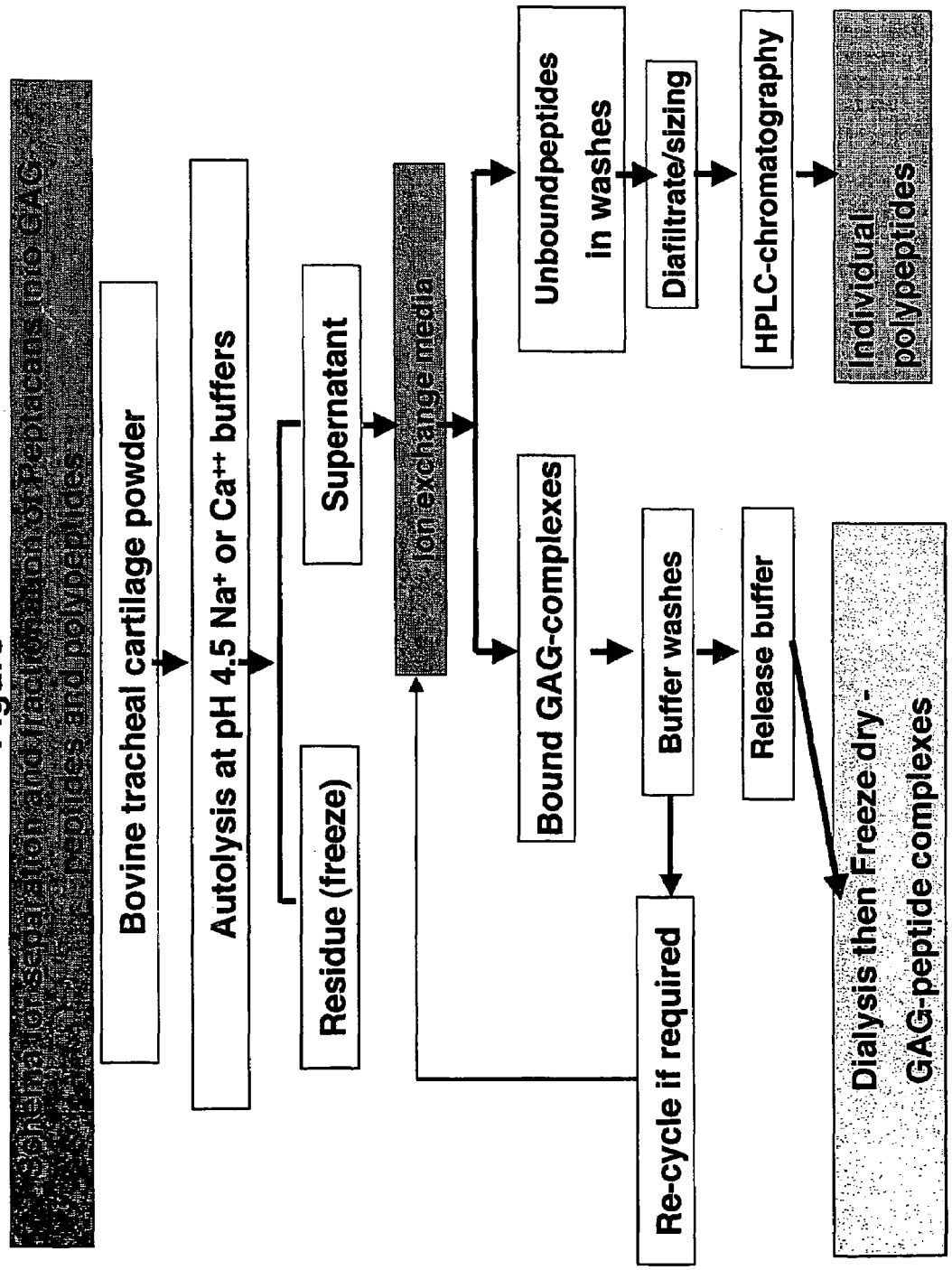
FIG. 14 provides a summary schema for the separation Peptacans such as CaP into its GAG-peptide (GAG-P) and polypeptides components using ion-exchange media.
Figure 15:
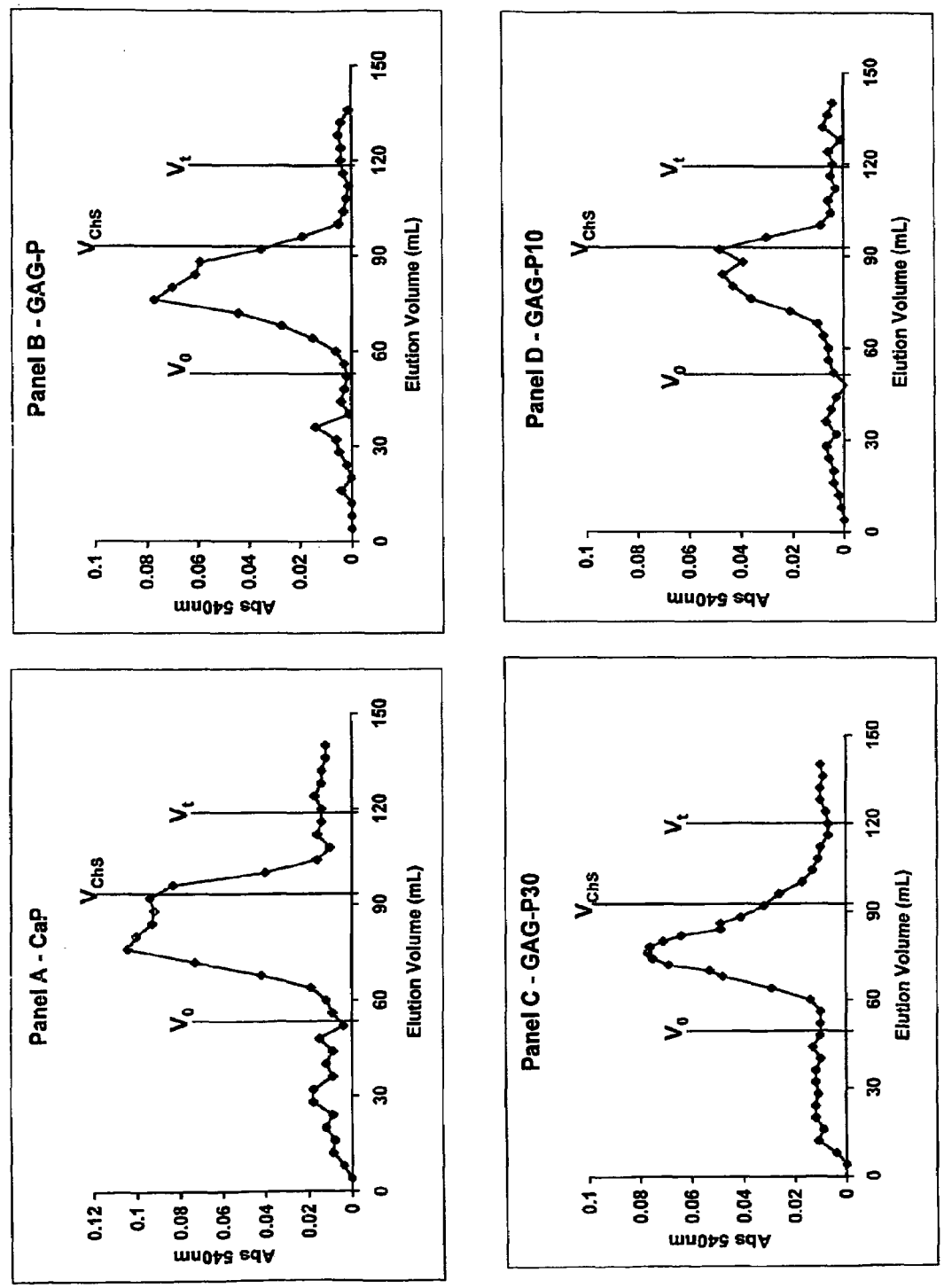
FIG. 15 provides Superdex-200 gel permeation chromatographic profiles of CaP (Panel A), GAG-P, prepared by from CaP by the ion exchange method (Panel B), GAG-P30, the retentate prepared from CaP using the 30 kDa TFF cut-off membrane (Panel C) and GAG-P 10 the dialysate obtained from the 30 kDa TFF cut-off experiment but retained after further ultrafiltration of the dialysate using a 10 kDa cut-off TFF membrane (Panel D). The column was eluted with 0.25M NaCl at a flow rate of 1.0 mL/minute. Fractions (1.0 mL) were collected and assayed for the levels of sulfated glycosaminoglycans using the method of Farndale et al. 1986 [Farndale R W, Buttle D J and Barrett A J. Improved quantitation and discrimination of sulfated glycosaminoglycans by use of dimethylmethylene blue. Biochim. Biophys. Acta: 883, 173–177, 1986]. Note that ultrafiltration of CaP through the 30 kDa membrane removes the majority of ChS present.
Figure 16:
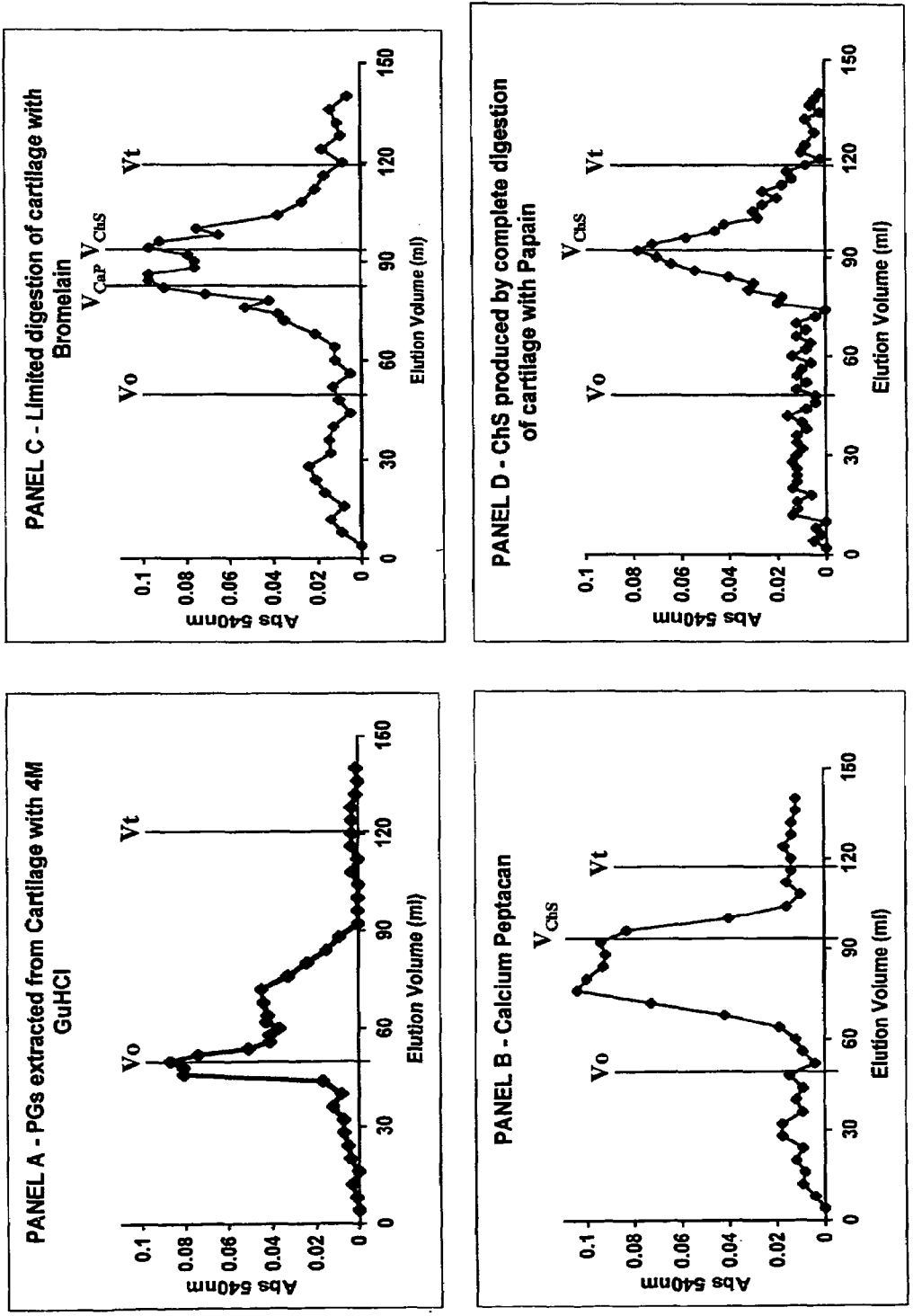
FIG. 16 provides Superdex-200 gel permeation chromatographic profiles of undegraded proteoglycans (PGs) extracted from bovine tracheal cartilage using 4M guanidium chloride (GuHCl) (Panel A), CaP (Panel B), the GAG-peptides produced by limited hydrolysis of bovine tracheal cartilage with bromelain (Panel C) and Chondroitin Sulfate (ChS) standard (Panel D). The column was eluted with 0.25M NaCl at a flow rate of 1.0 mL/minute. Fractions (1.0 mL) were collected and assayed for the levels of sulfated glycosaminoglycans using the method of Farndale et al, 1986 [Farndale R W, Buttle D J and Barrett A J. Improved quantitation and discrimination of sulfated glycosaminoglycans by use of dimethylmethylene blue. Biochim. Biophys. Acta: 883, 173–177, 1986]. Note that the GAG-peptides produced by limited hydrolysis with bromelain using the conditions described herein consist mainly of molecular species of sizes similar to CaP and ChS.

Using a connective tissue derived composition comprising a GAG-peptide complex and polypeptide mixture obtained by autolysis (CaP) as an example and the protocol shown schematically in FIG. 14, a calcium salt of a glycosaminoglycan peptide (GAG-P) consisting largely of 2 ChS chains covalently attached to a peptide stub and free of protein or peptides was obtained as confirmed by chemical analysis, PAGE and gel filtration chromatography. The TFF ultrafiltration method, using various membranes with 0.5 kDa, 1.0 kDa, 10 kDa and 30 kDa molecular weight cut off, also provided a means of partially purifying the products of cartilage autolysis and limited hydrolysis. However, the technique not only selectively removed proteins and peptides from the preparations, but also fractionated the GAG-peptides present according to the molecular size distribution (see FIG. 15). When the GAG-peptide complex polypeptide mixture was prepared from tracheal cartilage using acetic acid buffer and was subjected to the same ion exchange procedure to that shown in FIG. 16, a GAG-peptide complex containing 3 ChS chains was obtained.

It was also demonstrated that GAG-peptide complexes of the desired molecular size could be obtained from cartilage using the procedure of limited hydrolysis of cartilage. This was illustrated using the proteolytic enzyme, bromelain or by alkaline hydrolysis with sodium hydroxide as examples.

The inventor found that proteoglycans present in bovine tracheal cartilage were only partially degraded to ChS by bromelain. The other polyanionic species produced corresponding to GAG-peptide complexes of similar molecular size to those of CaP.

Figure 17:
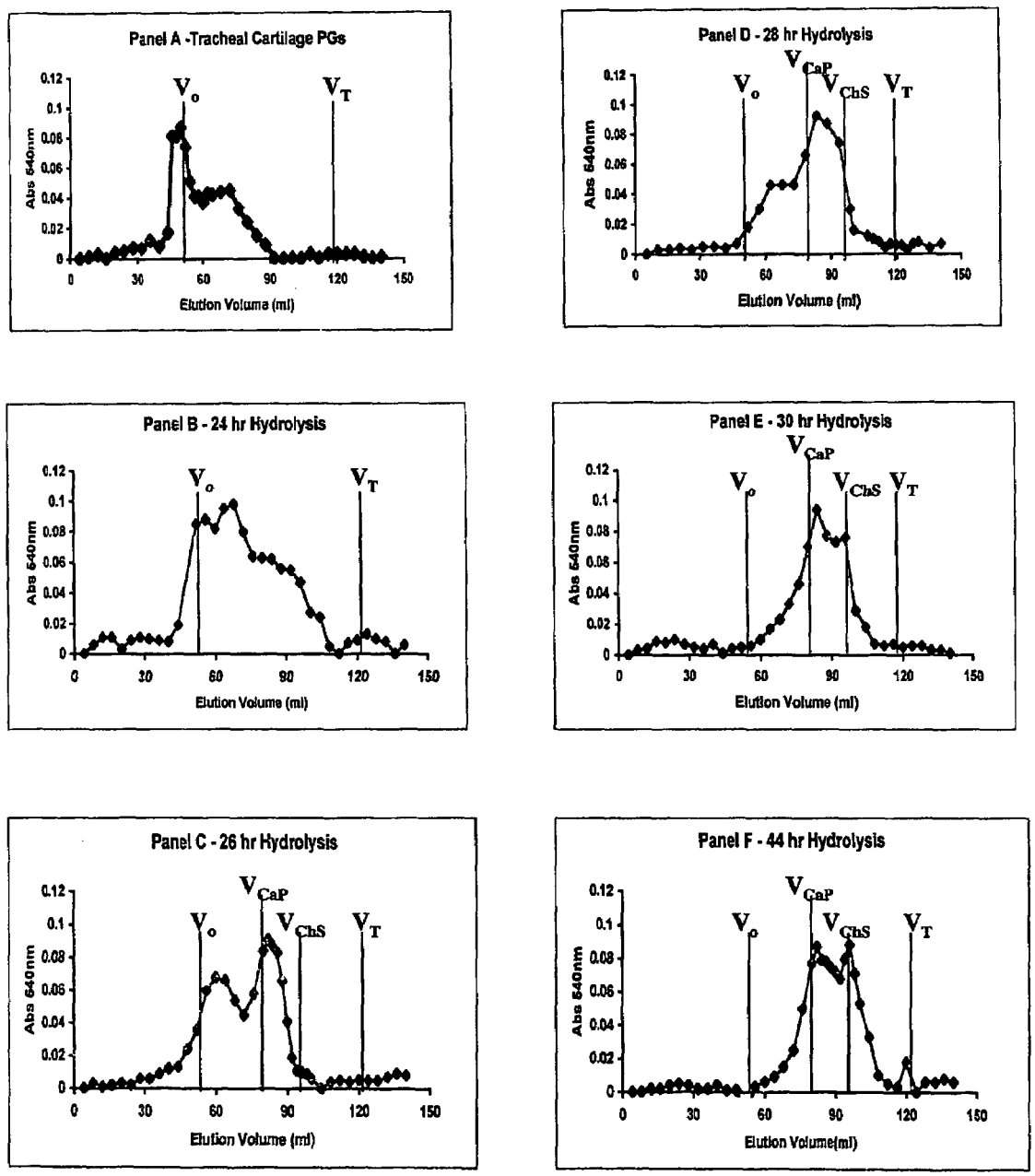
FIG. 17 provides a Superdex-200 gel permeation chromatographic profile of native proteoglycans (PGs) extracted from bovine tracheal cartilage using 4M Guanidium Chloride (GuHCl) (Panel A), the GAG-peptides produced by limited hydrolysis of bovine tracheal cartilage with 0.1% aqueous sodium hydroxide at 37° C., for 24 hours (Panel B), the GAG-peptides produced by limited hydrolysis of bovine tracheal cartilage with 0.1% aqueous sodium hydroxide at 37° C.; for 26 hours (Panel C), the GAG-peptides produced by limited hydrolysis of bovine tracheal cartilage with 0.1% aqueous sodium hydroxide at 37° C., for 28 hours (Panel D), the GAG-peptides produced by limited hydrolysis of bovine tracheal cartilage with 0.1% aqueous sodium hydroxide at 37° C., for 30 hours (Panel E), and the GAG-peptides produced by limited hydrolysis of bovine tracheal cartilage with 0.1% aqueous sodium hydroxide at 37° C., for 44 hours (Panel F). The column was eluted with 0.25M NaCl at a flow rate of 1.0 mL/minute. Fractions (1.0 mL) were collected and assayed for the levels of sulfated glycosaminoglycans using the method of Farndale et al, 1986 [Farndale R W, Buttle D J and Barrett A J. Improved quantitation and discrimination of sulfated glycosaminoglycans by use of dimethylmethylene blue. Biochim. Biophys. Acta: 883, 173–177, 1986]. Note that the GAG-peptides produced by the alkaline limited hydrolysis with sodium hydroxide for 30 hours consist mainly of molecular species of sizes similar to CaP and ChS.

Limited hydrolysis of bovine cartilage with solutions of aqueous sodium hydroxide were found to undergo a more complex pathway of breakdown with molecular species of similar size to CaP being generated between 26 and 44 hours at 37° C. However, the longer hydrolysis times were found to increase the proportions of ChS present (FIG. 17, panels C–F).

Even though these experiments have shown that bromelain or sodium hydroxide can be used to produce a GAG-peptide complex from cartilage with a molecular size similar to or greater than CaP, these preparations would appear to also contain an amount of single chain ChS. The smaller GAG species, including ChS could be removed from these mixtures using TFF ultra filtration with membranes of appropriate size molecular weight cut-offs.

Example 4

Characterisation of Glycosaminoglycan Peptides as Exemplified by GAG-PLH

| Assay | Result |
|---|---|
| material density (g/mL) | 1.03 |
| pH (10 mg/mL) | 6.75 |
| refractive index (100 mgs/mL) | 1.3450 |
| transmittance (10 mgs/mL) | 45.4% |
| total collagen peptides | 18% |
| total hexosamine | 2.5% |
| total sulfated glycosaminoglycans | 8% |

The glycosaminoglycan peptides obtained by limited hydrolysis of bovine tracheal cartilage or the residue remaining from the preparation of calcium peptacan were shown to be of similar molecular size distribution, although INR- 918R prepared by neutralisation with ascorbic acid appeared to be smaller than the other two preparations studied. Additional reactions, other than simply neutralisation, were also evident in the ascorbate neutralisation method as was indicated by the generation of fluorescent substances (activation at 335–340 nM and emission max at 400 nM) in the final products. On the other hand, the molecular sizes of the co-produced protein/polypeptides from the limited hydrolysis of cartilage or cartilage residual particles and neutralisation with ascorbate were larger (20,000 Da) than when acetic acid was used (17,000 Da) suggesting that the glycosidic linkages of the glycosaminoglycans in cartilage were more sensitive to ascorbate radicals cleavage than the proteins.

Example 5

(i) Topical Anti-inflammatory Activity of Cream Base

The GAG-peptides described in this application also demonstrated anti-inflammatory activity when applied topically in a cream base to human subjects. The results of a study undertaken with GAG-PLH are shown in Table 4.

The results of this anti-inflammatory study showed that 8 out of the 10 subjects who used the cream base containing GAG-PLH experienced a positive response, the remaining 2 subjects exhibiting equivalent activity to the cream base alone. The mean value and standard deviation for the 10 subjects who applied the cream base containing GAG-PLH to the erythema site was determined to be 3.04±0.82 while the corresponding values for the subjects applying cream base alone was, 2.59±0.88. Analysis of these data using the paired values for each subject (left or right arms) showed that the two cream treatments were statistically different at the $p<0.002$ probability level.

The above study served to demonstrate that the GAG-peptide complexes described herein were not only active in preventing inflammation and arthritis in animal models of arthritis when administered orally but were also active when applied topically to human subjects.

TABLE 4

Topical anti-inflammatory activity of Cream base with and without the addition of the Gly-cosaminoglycan preparation, GAG-PLH prepared by limited hydrolysis of cartilage. Decrease of Sodium Lauryl Sulfate induced erythema determined from difference on day 1 (tm1) to day 8 (tm4). In 8 of 10 subjects Cream base + GAG-PLH showed lower scores than Cream base alone demonstrating higher anti-inflammatory activity with GAG-PLH.*

TABLE 4-continued

Test Subject No: 745

| Left Arm Cream Base | | | | | | | | Right Arm Cream Base + GAG-PLH | | | | | | | |
|---|---|---|---|---|---|---|---|---|---|---|---|---|---|---|---|
| ? | 3 | 5 | 2 | 5 | 4 | ? | 4 | ? | ? | 5 | 3 | 3 | ? | 4 | 6 | 4 | 6 |
| ? | 3 | 5 | 1 | 5 | 3 | ? | 3 | 5 | ? | +1 | 0 | 2 | 4 | 3 | 5 | 3 | 5 |
| ? | 1 | 3 | 1 | 3 | 2 | ? | 2 | ? | ? | +1 | ? | 1 | 2 | 1 | 4 | 2 | 4 |
| ? | -1 | 0 | 1 | ? | 1 | ? | ? | ? | ? | ? | 0 | -1 | 2 | 1 | 5 | 1 | 5 |

Mean Change

Test Subject No: 173

| Left Arm Cream Base + GAG-PLH | | | | | | | | Right Arm Cream Base | | | | | | | |
|---|---|---|---|---|---|---|---|---|---|---|---|---|---|---|---|
| ? | -1 | 2 | 2 | 4 | 3 | 5 | 4 | 6 | ? | +1 | 2 | 2 | 4 | 3 | ? | 4 | 6 |
| ? | -1 | 2 | 2 | 4 | 2 | 4 | 3 | 5 | ? | 2 | 1 | +1 | 2 | 2 | 4 | 3 | 5 |
| ? | -1 | 2 | 1 | 3 | 1 | ? | 2 | 4 | ? | 2 | 1 | +1 | 2 | 1 | 3 | 2 | 4 |
| ? | 0 | 0 | 0 | 0 | +1 | ? | +1 | 2 | ? | 0 | 0 | 0 | 0 | 1 | 3 | 1 | 5 |
|   | ? |   | ? |   | -3 |   | -4 |   |   | -2 |   | ? |   | -2 |   | -3 |

Mean Change

Test Subject No: 180

| Left Arm Cream Base + GAG-PLH | | | | | | | | Right Arm Cream Base | | | | | | | |
|---|---|---|---|---|---|---|---|---|---|---|---|---|---|---|---|
| ? | 1 | 3 | 3 | ? | 3 | 5 | 3 | 5 | ? | +1 | 2 | 2 | 4 | 2 | 4 | 3 | 5 |
| ? | 1 | 3 | 2 | 1 | 3 | 5 | 3 | 5 | ? | ? | 1 | +1 | 2 | 2 | 4 | 2 | 4 |
| ? | 1 | 3 | 1 | 3 | 2 | 4 | 2 | 4 | ? | ? | 1 | +1 | 2 | 1 | 5 | 2 | 4 |
| ? | 2 | 3 | -1 | ? | 1 | 3 | 1 | 3 | ? | 0 | 0 | 0 | 1 | +1 | 2 | 1 | 3 |
|   | -2 |   | +3 |   | -2 |   | 2 |   |   | -2 |   | ? |   | -2 |   | -2 |

Mean Change

Test Subject No: 336

| Left Arm Cream Base | | | | | | | | Right Arm Cream Base + GAG-PLH | | | | | | | |
|---|---|---|---|---|---|---|---|---|---|---|---|---|---|---|---|
| ? | +1 | 2 | 2 | 4 | 3 | 5 | 3 | 5 | ? | +1 | 2 | 2 | 4 | 3 | 5 | 5 | 6 |
| ? | 2 | 1 | 2 | 4 | 2 | 4 | 2 | 4 | ? | ? | 1 | +1 | 2 | 2 | 4 | 2 | 4 |
| ? | 2 | 1 | +1 | 5 | -1 | 2 | -1 | 2 | ? | ? | 1 | +1 | 2 | 1 | ? | 1 | 0 |
| ? | 0 | 0 | 2 | 1 | -1 | 2 | 1 | 3 | ? | 0 | 0 | 0 | 0 | -1 | ? | 1 | 3 |
|   | -2 |   | -3 |   | -3 |   | 2 |   |   | -2 |   | ? |   | ? |   | -2 |

Mean Change

Test Subject No: 328

| Left Arm Cream Base | | | | | | | | Right Arm Cream Base + GAG-PLH | | | | | | | |
|---|---|---|---|---|---|---|---|---|---|---|---|---|---|---|---|
| ? | 2 | 4 | 2 | 4 | 2 | 4 | ? | 5 | ? | 2 | 4 | 2 | 4 | 2 | 4 | ? | 5 |
| ? | 0 | 0 | -1 | 2 | +1 | 2 | ? | 4 | ? | 1 | 3 | 1 | 3 | 2 | 4 | ? | 1 |
| ? | 0 | 0 | 1 | 1 | ? | 1 | 0 | 2 | ? | ? | 1 | ? | 1 | -1 | 2 | ? | 1 |
| ? | 0 | 0 | 0 | 0 | ? | 0 | 0 | 3 | ? | 0 | 0 | 0 | 0 | 0 | 0 | 0 | 0 |
|   | ? |   | -4 |   | -4 |   | -3 |   |   | -4 |   | -4 |   | ? |   | -3 |

Mean Change

TABLE 4-continued

Test Subject No: 320

Left Arm    Cream Base + GAG-PLH

| ? | -1 | 2 | 3 | 5 | 4 | ? | 3 | 5 |
|---|----|---|---|---|---|---|---|---|
| ? | 2  | 1 | -1| 2 | 1 | ? | 1 | 3 |
| ? | 2  | 1 | 9 | 1 | -1| 2 | 1 | 3 |
| ? | 0  | 0 | 0 | 0 | 0 | 0 | ? | 1 |

| 2 | -5 | -6 | -4 |
|---|----|----|----|

| Mean Change | ? | ? |

Right Arm    Cream Base

| ? | 1 | ? | 3 | 5 | 2 | 2 | -1 | 2 |
|---|---|---|---|---|---|---|----|---|
| ? | 2 | ? | 2 | 1 | -1| 2 | -1 | 2 |
| ? | 0 | 0 | ? | 1 | -1| 2 | -1 | 2 |
| ? | 0 | 0 | 0 | 0 | 0 | 0 | 0  | 0 |

| 3 | 5 | ? | ? |
|---|---|---|---|

| Mean Change | ? | ? |

Test Subject No: 327

Left Arm    Cream Base

| ? | -1 | 2 | 2 | 4 | 3 | 5 | 4 | 6 |
|---|----|---|---|---|---|---|---|---|
| ? | 2  | 2 | +1| 2 | 2 | 4 | ? | 4 |
| ? | 0  | 0 | +1| ? | 1 | 3 | 1 | 3 |
| ? | 0  | 0 | ? |   | -1| ? | -1| 2 |

| -2 | -3 | -3 | 4 |
|----|----|----|---|

| Mean Change | ? | ? |

Right Arm    Cream Base + GAG-PLH

| ? | ? | 4 | ? | 4 | 3 | ? | 4 | 5 |
|---|---|---|---|---|---|---|---|---|
| ? | 0 | 3 | ? | 1 | -1| 2 | 1 | ? |
| ? | 0 | 1 | 0 | 0 | 2 | ? | ? | ? |
| ? | 0 | 0 | 0 | 0 | 0 | 0 | ? | 1 |

| ? | -4 | ? | ? |
|---|----|---|---|

| Mean Change | ? | ? |

*ERYTHEMA SCORING SYSTEM

One hour after removal of all patches and before application of the topical medications all sites were evaluated for response using the scoring and corresponding numerical value shown below:

| SCORE | VALUE |
|-------|-------|
| 0 = no evidence of an effect | 0 |
| ? = query | 1 |
| +1 = minimal, faint, uniform or spotty erythema | 2 |
| 1 = pink uniform erythema covering most or all of the contact site | 3 |
| 2 = pink-red erthyma visibly uniform over entire contact site | 4 |
| 3 = bright red erthyma with or without petechlas or papules | 5 |
| 4 = deep red erythema with or without vealculation or weeping | 6 |

The same evaluation was completed at each subsequent time point (t), that is 2, 4, and 8 days after initial application on day 1.

(ii) Reports by Subjects Using a Topical Composition Comprising a Connective Tissue Derived Composition According to the Present Invention:

1) Mrs R G: Thrice daily topical application of topical composition to hands relieved the pain and stiffness due to osteoarthritis in both hands.
2) Mr M Q: Daily application of topical composition for 2 weeks relieved the pain from tendon stain/injury in thumb of right hand.
3) Mrs J M: Twice daily topical application topical composition to left hand partially relieved the pain and flexibility of thumb joint, normally stiff due to osteoarthritis.
4) Mrs J E: Daily application of topical composition to face reduced the appearance and discomfort normally experienced from Rosacea.
5) Male Patient of Dr. M M: reported positive effects of daily application of topical composition to Rosacea over upper neck area.
6) Mr G E: Regular application of topical composition to lower calf of legs reduced the intensity and irritation caused by long standing dermatitis.
7) Mrs N W-G: Immediate application, followed by daily application of topical composition to burn wound caused by electric hot plate provided pain relief and accelerated skin healing.
8) Son of S C: Showed 24 hour recovery from sun-burn following immediate topical application of topical composition to the affected area.
9) Ms R B: Twice daily topical application to face and neck provided decreased dryness, and increased firmness and smoothness of the skin.
10) Mrs D A: Noticed decrease in crows feet around eyes and more youthful appearance of the skin after several weeks application.
11) Mrs C B: Observed that dryness and redness of skin around nose was decreased after several weeks application of the cream. On cessation of application the redness and dryness returned but were eliminated by subsequent application of the preparation.
12) Ms N W: Skin seems smoother and more supple after application of cream twice daily for two weeks.
13) Mr. R H: After many years exposure of his face to the Queensland (Australia) sun he noticed a definite improvement in skin texture and smoothness within a week of applying the cream twice daily.
14) Mrs. R H: As a regular player and captain of the local golf club she had sustained considerable photo-damage to her skin but reported that the cream appear to reduce the damage and provided superior appearance to her skin to any other product she had tried over the past 20 years.

15) Mrs J F: considered that her skin of her face and neck was more youthful in appearance and felt smoother after using the cream for several weeks.

Aging of the skin occurs by two main pathways. The first called intrinsic aging arises from the physiological process of cell degeneration and loss of viability as a function of time probably due to accumulating defects to DNA and inherent genetic factors. This process occurs in both sun-exposed and non-exposed skin. The skin is generally seen clinically as a shiny atrophic easily damaged surface with increase transparency allowing the underlying tissue and vascular structures to become visually apparent. Actinic damage is the second pathway for aging of skin and is due to the direct effects of ultraviolet radiation most commonly in the form of sunlight causing accumulating damage to cells and the components of the extracellular matrix. Clinically the skin appears sallow with surface mottling, and a coarse thickened texture and will often sage due to impairment to the supportive elastic and collagen fibres (solar elastosis). Photo-damage to skin is the major cause of wrinkling but is exacerbated by the chronologically determined aging process as well as, for example, the number of years of smoking. During solar elastosis the abnormal elastic fibers deposited in the skin are associated by the accumulation of large amounts of versican proteoglycans. This enhanced synthesis of versican and abnormal elastic fibers are concomitant with a corresponding decline in the biosynthesis of collagen and collagen associated proteoglycans such as decorin, biglycan and fibromodulin.

The preparations described in this invention contain a mixture of polypeptides, and glycosaminoglycan peptide complexes derived from the extracellular matrix of connective tissues. The molecules appear to influence the metabolism of connective tissues cells such as those contained in the various layers of skin beneath the stratum corneum and are thought to provide the nourishment and 'feed-back control' to sustain the viability and maintain the normal cellular processes required to preserve the youthful characteristics of skin, whose normal metabolism has become impaired due to the chronological and photo aging mechanisms described above.

In addition the presence in some of the preparations of the present invention of free ascorbic acid and the complexes it forms with amino acids and polypeptides by the Maillard reaction, which are all well known to be anti-oxidants and antagonists of photo aging, preferably serve to retard or even reverse tissue damage accumulated due to both the intrinsic and extrinsic aging of skin.

The invention will now be further described by the following numbered paragraphs:

1. A topical composition comprising a connective tissue derived composition comprising one or more GAG-peptide complex in combination with a dermatalogically acceptable vehicle, wherein at least one GAG-peptide complex comprises 2 or 3 GAG chains.

2. The topical composition according to paragraph 1, wherein said connective tissue derived composition is present in an amount of about 0.1% to about 15% by weight of the topical composition.

3. The topical composition according to paragraph 1, wherein said connective tissue derived composition is present in an amount of about 5% to about 10% by weight of the topical composition.

4. The topical composition according to paragraph 1, wherein said connective tissue derived composition is present in an amount of about 5% by weight of the topical composition.

5. The topical composition according to paragraph 1, wherein said connective tissue derived composition is present in an amount of about 10% by weight of the topical composition.

6. The topical composition according to paragraph 1 further comprising an amount of hyaluronic acid, chondroitin sulphate, collagen glucosamine, keratan sulphate, dermatan sulphate, vitamin C, green tea extract, shea butter, grape-seed extract, aloe extract or mixtures thereof.

7. The topical composition according to paragraph 1, wherein the composition provides a skin care benefit.

8. The topical composition according to paragraph 7, wherein the skin care benefit comprises at least one of the following: reducing skin wrinkling, sagging, dryness, irritation, inflammation, swelling, photo-damage or scarring, boosting collagen and elastin deposition in skin, enhancing skin repair, improving skin texture, smoothness or firmness, or combinations thereof.

9. The topical composition according to paragraph 1, wherein the composition provides a subdermal tissue benefit.

10. The topical composition according to paragraph 9, wherein the subdermal tissue benefit comprises at least one of the following: reducing inflammation, trauma, damage, irritation, allergic reaction, swelling, pain or stiffness in a subdermal tissue, or combinations thereof.

11. A method of providing at least one skin care benefit to a subject in need thereof, the method comprising applying a topical composition comprising a connective tissue derived composition comprising one or more GAG-peptide complex in combination with a dermatalogically acceptable vehicle, wherein at least one GAG-peptide complex comprises 2 or 3 GAG chains.

12. The method according to paragraph 11, wherein the skin care benefit comprises at least one of the following: reducing wrinkling, sagging, dryness, irritation, inflammation, swelling, photo damage or scarring of the skin, boosting collagen and elastin deposition in skin, enhancing skin repair, improving skin texture, smoothness or firmness, or combinations thereof.

13. A method of providing at least one subdermal tissue benefit to a subject in need thereof, the method comprising applying a topical composition comprising a connective tissue derived composition comprising one or more GAG-peptide complex in combination with a dermatalogically acceptable vehicle, wherein at least one GAG-peptide complex comprises 2 or 3 GAG chains.

14. The method according to paragraph 13, wherein the subdermal tissue benefit comprises at least one of the following: reducing inflammation, trauma, damage, irritation, allergic reaction, swelling, pain or stiffness in a subdermal tissue, or combinations thereof.

15. Use of a topical composition comprising a connective tissue derived composition comprising one or more GAG-peptide complex in combination with a dermatalogically acceptable vehicle, wherein at least one GAG-peptide complex comprises 2 or 3 GAG chains for providing at least one skincare benefit to a subject in need thereof.

16. Use of a topical composition comprising a connective tissue derived composition comprising one or more GAG-peptide complex in combination with a dermatalogically acceptable vehicle, wherein at least one GAG-peptide complex comprises 2 or 3 GAG chains for providing at least one subdermal tissue benefit to a subject in need thereof.

17. Use of one or more GAG-peptide complex comprising two or three GAG-chains in a topical composition for providing at least one skincare benefit to a subject in need thereof.

18. Use of one or more GAG-peptide complex comprising two or three GAG-chains in a topical composition for providing at least one or subdermal tissue benefit to a subject in need thereof.

19. Use according to paragraph 17, wherein the skin care benefit comprises at least one of the following: reducing wrinkling, sagging, dryness, irritation, inflammation, swelling, photo-damage or scarring of the skin, boosting collagen deposition in skin, enhancing tissue repair, improving skin texture, smoothness or firmness, or combinations thereof.

20. Use according to paragraph 18, wherein the subdermal tissue benefit comprises at least one of the following: reducing inflammation, trauma, damage, irritation, allergic reaction, swelling, pain or stiffness in a subdermal tissue, or combinations thereof.

The invention claimed is:

1. A topical composition comprising a connective tissue derived composition comprising one or more glycosaminoglycan-peptide (GAG-peptide) complexes in combination with a dermatalogically acceptable vehicle, wherein the at least one GAG-peptide complex comprises 2 GAG chains and has a molecular weight of about 32,000 Da.

2. The topical composition according to claim 1, wherein said connective tissue derived composition is present in an amount of about 0.1% to about 15% by weight of the topical composition.

3. The topical composition according to claim 1, wherein said connective tissue derived composition is present in an amount of about 5% to about 10% by weight of the topical composition.

4. The topical composition according to claim 1, wherein said connective tissue derived composition is present in an amount of about 5% by weight of the topical composition.

5. The topical composition according to claim 1, wherein said connective tissue derived composition is present in an amount of about 10% by weight of the topical composition.

6. The topical composition according to claim 1 further comprising an amount of hyaluronic acid, chondroitin sulphate, collagen glucosamine, keratan sulphate, dermatan sulphate, vitamin C, green tea extract, shea butter, grapeseed extract, aloe extract of mixtures thereof.

7. The topical composition according to claim 1, wherein the composition provides a skin care benefit comprising at least one of the following: reducing skin wrinkling, sagging, dryness, irritation, inflammation, swelling, enhancing skin repair, improving skin texture, smoothness or firmness, or combinations thereof.

8. A method of providing at least one skin care benefit selected from the group consisting of reducing wrinkling, sagging, dryness, irritation, inflammation, swelling, improving skin texture, smoothness or firmness, or combinations thereof to a subject in need thereof, the method comprising applying a topical composition comprising a connective tissue derived composition comprising one or more GAG-peptide complex in combination with a dermatalogically acceptable vehicle, wherein at least one GAG-peptide complex comprises 2 or 3 GAG chains.

9. A method of using a topical composition comprising a connective tissue derived composition comprising one or more GAG-peptide complex in combination with a dermatalogically acceptable vehicle, wherein at least one GAG-peptide complex comprises 2 or 3 GAG chains for providing at least one skincare benefit or subdermal tissue benefit to a subject in need thereof.

* * * * *

UNITED STATES PATENT AND TRADEMARK OFFICE
CERTIFICATE OF CORRECTION

PATENT NO.       : 7,211,648 B2
APPLICATION NO.  : 11/130470
DATED            : May 1, 2007
INVENTOR(S)      : Ghosh It is certified that error appears in the above-identified patent and that said Letters Patent is hereby corrected as shown below:

Col. 35 - line 22 to Col. 39-40
Replace Table 4 as follows:

Table 4: Topical anti-inflammatory activity of Cream base with and without the addition of the Glycosaminoglycan preparation, GAG-PLH prepared by limited hydrolysis of cartilage. Decrease of Sodium Lauryl Sulfate induced erythema determined from difference on day 1 (t=1) to day 8 (t=4). In 8 of 10 subjects Cream base + GAG-PLH showed lower scores than Cream base alone demonstrating higher anti-inflammatory activity with GAG-PLH.*

Test Subject No. 55

| | Left Arm | Cream Base | | | | | Right Arm | Cream Base + GAG-PLH | | | |
|---|---|---|---|---|---|---|---|---|---|---|---|
| t=1 | ? 1 | +1 2 | 1 3 | 1 3 | | t=1 | ? 1 | +1 2 | 1 3 | 2 4 |
| t=2 | 0 0 | ? 1 | +1 2 | +1 2 | | t=2 | 0 0 | ? 1 | +1 2 | +1 2 |
| t=3 | 0 0 | ? 1 | +1 2 | +1 2 | | t=3 | 0 0 | ? 1 | ? 1 | ? 1 |
| t=4 | 0 0 | ? 1 | +1 2 | +1 2 | | t=4 | 0 0 | 0 0 | ? 1 | ? 1 |
| | -1 | -1 | -1 | -1 | | | -1 | -2 | -2 | -3 |
| Mean Change: t=1 to t=4 | -1 | | | | | Mean Change: t=1 to t=4 | -2 | | | |

Test Subject No: 181

| | Left Arm | Cream Base | | | | | Right Arm | Cream Base + GAG-PLH | | | |
|---|---|---|---|---|---|---|---|---|---|---|---|
| t=1 | 2 4 | 3 5 | 3 5 | 2 4 | | t=1 | 1 3 | 2 4 | 3 5 | 2 4 |
| t=2 | +1 2 | 2 4 | 3 5 | 3 5 | | t=2 | ? 1 | 2 4 | 3 5 | 3 5 |
| t=3 | +1 2 | 2 4 | 2 4 | 2 4 | | t=3 | ? 1 | +1 2 | 1 3 | 2 4 |
| t=4 | +1 2 | 1 3 | 2 4 | 2 4 | | t=4 | 0 0 | +1 2 | 1 3 | 2 4 |
| | -2 | -2 | -1 | 0 | | | -3 | -2 | -2 | 0 |
| Mean Change: t=1 to t=4 | -1.3 | | | | | Mean Change: t=1 to t=4 | -1.8 | | | |

UNITED STATES PATENT AND TRADEMARK OFFICE
CERTIFICATE OF CORRECTION

PATENT NO. : 7,211,648 B2
APPLICATION NO. : 11/130470
DATED : May 1, 2007
INVENTOR(S) : Ghosh It is certified that error appears in the above-identified patent and that said Letters Patent is hereby corrected as shown below:

Test Subject No. 739

Left Arm — Cream Base + GAG-PLH

| | t=1 | t=2 | t=3 | t=4 | | |
|---|---|---|---|---|---|---|
| | 1  3 | 0  0 | 0  0 | 0  0 | -3 | |
| | 2  4 | +1  2 | ?  1 | 0  0 | -4 | |
| | 2  4 | 1  3 | +1  2 | +1  2 | -2 | |

Mean Change: t=1 to t=4   -3

Right Arm — Cream Base

| | t=1 | t=2 | t=3 | t=4 | |
|---|---|---|---|---|---|
| | 2  4 | ?  1 | 0  0 | 0  0 | -4 |
| | 2  4 | +1  2 | +1  2 | ?  1 | -3 |
| | 2  4 | 2  4 | 1  3 | 1  3 | -1 |

Mean Change: t=1 to t=4   -2.7

Test Subject No. 746

Left Arm — Cream Base

| | t=1 | t=2 | t=3 | t=4 | |
|---|---|---|---|---|---|
| | 3  5 | 3  5 | 1  3 | +1  2 | -3 |
| | 3  5 | 3  5 | 1  3 | 1  3 | -2 |
| | 4  6 | 3  5 | 2  4 | 1  3 | -3 |
| | 4  6 | 3  5 | 2  4 | +1  2 | -4 |

Mean Change: t=1 to t=4   -3

Right Arm — Cream Base + GAG-PLH

| | t=1 | t=2 | t=3 | t=4 | |
|---|---|---|---|---|---|
| | 3  5 | +1  2 | +1  2 | ?  1 | -4 |
| | 3  5 | 2  4 | 1  3 | +1  2 | -3 |
| | 4  6 | 3  5 | 2  4 | 1  3 | -3 |
| | 4  6 | 3  5 | 2  4 | 1  3 | -3 |

Mean Change: t=1 to t=4   -3.3

Test Subject No: 173

Left Arm — Cream Base + GAG-PLH

| | t=1 | t=2 | t=3 | t=4 | |
|---|---|---|---|---|---|
| | +1  2 | +1  2 | +1  2 | 0  0 | -2 |
| | 2  4 | 2  4 | 1  3 | 0  0 | -4 |
| | 3  5 | 2  4 | 1  3 | +1  2 | -3 |
| | 4  6 | 3  5 | 2  4 | +1  2 | -4 |

Mean Change: t=1 to t=4   -3.3

Right Arm — Cream Base

| | t=1 | t=2 | t=3 | t=4 | |
|---|---|---|---|---|---|
| | +1  2 | ?  1 | ?  1 | 0  0 | -2 |
| | 2  4 | +1  2 | +1  2 | 0  0 | -4 |
| | 3  5 | 2  4 | 1  3 | 1  3 | -2 |
| | 4  6 | 3  5 | 2  4 | 1  3 | -3 |

Mean Change: t=1 to t=4   -2.8

Test Subject No: 180

Left Arm — Cream Base + GAG-PLH

| | t=1 | t=2 | t=3 | t=4 | |
|---|---|---|---|---|---|
| | 1  3 | 1  3 | 1  3 | ?  1 | -2 |
| | 3  5 | 2  4 | 1  3 | +1  2 | -3 |
| | 3  5 | 3  5 | 2  4 | 1  3 | -2 |
| | 3  5 | 3  5 | 2  4 | 1  3 | -2 |

Mean Change: t=1 to t=4   -2.3

Right Arm — Cream Base

| | t=1 | t=2 | t=3 | t=4 | |
|---|---|---|---|---|---|
| | +1  2 | ?  1 | ?  1 | 0  0 | -2 |
| | 2  4 | +1  2 | +1  2 | ?  1 | -3 |
| | 2  4 | 2  4 | 1  3 | +1  2 | -2 |
| | 3  5 | 2  4 | 2  4 | 1  3 | -2 |

Mean Change: t=1 to t=4   -2.3

UNITED STATES PATENT AND TRADEMARK OFFICE
CERTIFICATE OF CORRECTION

PATENT NO. : 7,211,648 B2
APPLICATION NO. : 11/130470
DATED : May 1, 2007
INVENTOR(S) : Ghosh Page 3 of 4

It is certified that error appears in the above-identified patent and that said Letters Patent is hereby corrected as shown below:

UNITED STATES PATENT AND TRADEMARK OFFICE
CERTIFICATE OF CORRECTION

| | | |
|---|---|---|
| PATENT NO. | : 7,211,648 B2 | Page 4 of 4 |
| APPLICATION NO. | : 11/130470 | |
| DATED | : May 1, 2007 | |
| INVENTOR(S) | : Ghosh | |

It is certified that error appears in the above-identified patent and that said Letters Patent is hereby corrected as shown below:

Test Subject No. 327

| Left Arm | Cream Base | | | | | | | Right Arm | Cream Base + GAG-PLH | | | | | | |
|---|---|---|---|---|---|---|---|---|---|---|---|---|---|---|---|
| t=1 | +1 | 2 | 2 | 4 | 3 | 5 | 4 | 6 | t=1 | ? | 1 | 2 | 4 | 3 | 5 | 4 | 6 |
| t=2 | ? | 1 | +1 | 2 | 2 | 4 | 2 | 4 | t=2 | 0 | 0 | ? | 1 | +1 | 2 | 1 | 3 |
| t=3 | 0 | 0 | +1 | 2 | 1 | 3 | 1 | 3 | t=3 | 0 | 0 | 0 | 0 | ? | 1 | ? | 1 |
| t=4 | 0 | 0 | ? | 1 | +1 | 2 | +1 | 2 | t=4 | 0 | 0 | 0 | 0 | 0 | 0 | ? | 1 |
| | -2 | | -3 | | -3 | | -4 | | -1 | | -4 | | -5 | | -5 |
| Mean Change: t=1 to t=4 | -3 | | | | | | | Mean Change: t=1 to t=4 | -3.8 | | | | | | |

**\*ERYTHEMA SCORING SYSTEM**

One hour after removal of all patches and before application of the topical medications all sites were evaluated for response using the scoring and corresponding numerical value shown below:

| SCORE | VALUE |
|---|---|
| 0 = no evidence of an effect | 0 |
| ? = query | 1 |
| +1 = minimal, faint, uniform or spotty erythema | 2 |
| 1 = pink uniform erythema covering most or all of the contact site | 3 |
| 2 = pink-red erythema visibly uniform over entire contact site | 4 |
| 3 = bright red erythema with or without petechias or papules | 5 |
| 4 = deep red erythema with or without vesiculation or weeping | 6 |

The same evaluation was completed at each subsequent time point (t), that is 2, 4, and 8 days after initial application on day 1.

Signed and Sealed this

Eleventh Day of December, 2007

JON W. DUDAS
*Director of the United States Patent and Trademark Office*